United States Patent
Gibelin et al.

(10) Patent No.: US 12,428,614 B2
(45) Date of Patent: Sep. 30, 2025

(54) BIOPHARMACEUTICAL LIQUID RESERVOIR WITH MECHANICAL MEMBER INCLUDING ROTATING AND STATIONARY SETS OF PARTS

(71) Applicant: SARTORIUS STEDIM FMT SAS, Aubagne (FR)

(72) Inventors: Jérémy Gibelin, Signes (FR); David Bourseaux, Allauch (FR); Yanis Loiselet, Ceyreste (FR)

(73) Assignee: Sartorius Stedim FMT SAS, Aubagne (FR)

( * ) Notice: Subject to any disclaimer, the term of this patent is extended or adjusted under 35 U.S.C. 154(b) by 1100 days.

(21) Appl. No.: 17/299,936

(22) PCT Filed: Nov. 25, 2019

(86) PCT No.: PCT/FR2019/000191
§ 371 (c)(1),
(2) Date: Jun. 4, 2021

(87) PCT Pub. No.: WO2020/115372
PCT Pub. Date: Jun. 11, 2020

(65) Prior Publication Data
US 2022/0049201 A1    Feb. 17, 2022

(30) Foreign Application Priority Data
Dec. 6, 2018    (FR) ...................................... 1872448

(51) Int. Cl.
*C12M 1/00*    (2006.01)
*A61J 1/10*    (2006.01)
(Continued)

(52) U.S. Cl.
CPC ............ *C12M 23/14* (2013.01); *C12M 23/34* (2013.01); *C12M 25/16* (2013.01); *C12M 27/04* (2013.01); *C12M 37/04* (2013.01); *A61J 1/10* (2013.01)

(58) Field of Classification Search
None
See application file for complete search history.

(56) References Cited

U.S. PATENT DOCUMENTS

| | | | | |
|---|---|---|---|---|
| 3,489,469 A | * | 1/1970 | Stratienko | F16J 15/40 366/331 |
| 5,385,546 A | * | 1/1995 | Kriesel | A61J 1/2089 604/82 |
| 5,676,472 A | * | 10/1997 | Solomon | B25J 21/005 384/480 |

OTHER PUBLICATIONS

English translation of Written Opinion of the International Searching Authority issued in PCT/FR2019/000191 and dated Feb. 5, 2020.

(Continued)

*Primary Examiner* — William H. Beisner
(74) *Attorney, Agent, or Firm* — Heslin Rothenberg Farley and Mesiti, PC; Victor A. Cardona, Esq.

(57) ABSTRACT

A biopharmaceutical liquid reservoir, includes a bag forming an inner storage space for storing a biopharmaceutical liquid, a mechanical member located at a wall of the bag, having: a stationary set of parts that is stationary with respect to the wall of the bag, a rotating set of parts rotating about an axis of rotation with respect to the stationary set, a bearing located between the two sets and, inside the bag, a communication passage: separating the bearing from the inner storage space, including one or more changes of direction, being formed by a portion of the parts of the rotating set located opposite a portion of the parts of the stationary set.

37 Claims, 15 Drawing Sheets

(51) Int. Cl.
    *C12M 1/04*         (2006.01)
    *C12M 1/12*         (2006.01)

(56)         References Cited

OTHER PUBLICATIONS

Search Report for French Patent Application No. 1872448 mailed on Sep. 13, 2019.
International Search Report (and English translation) and Written Opinion of the International Searching Authority for International Application No. PCT/FR2019/000191 mailed on Feb. 5, 2020.

\* cited by examiner

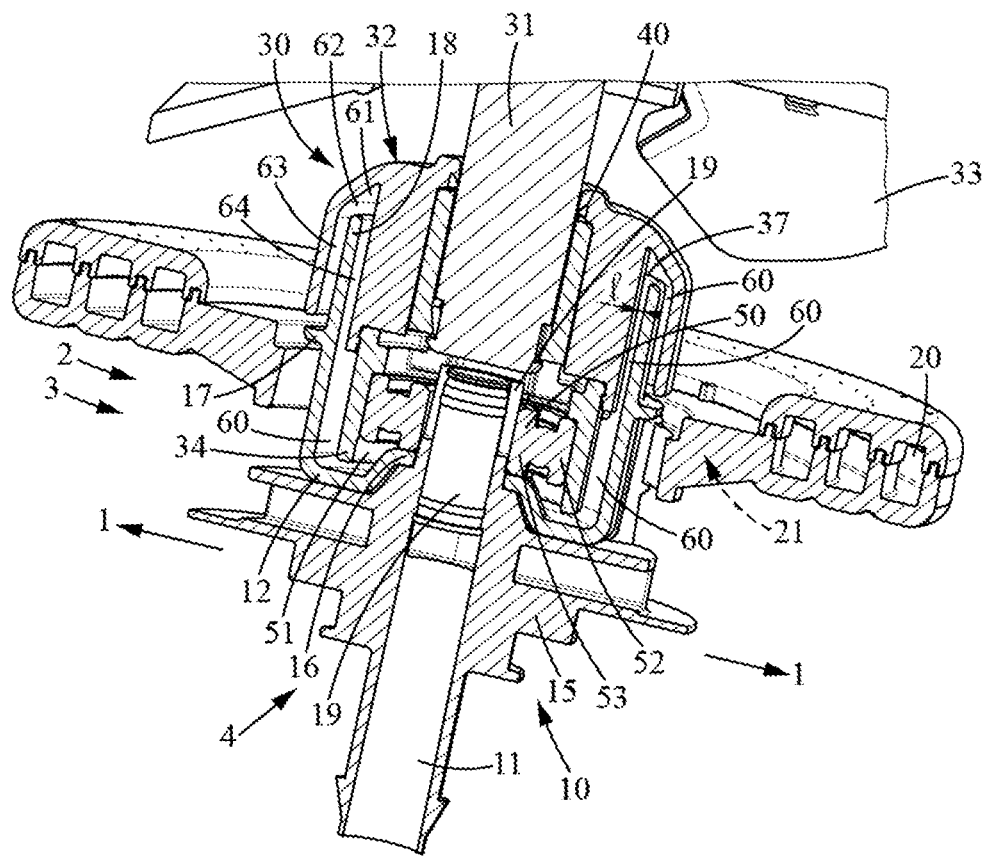
[Fig. 1]
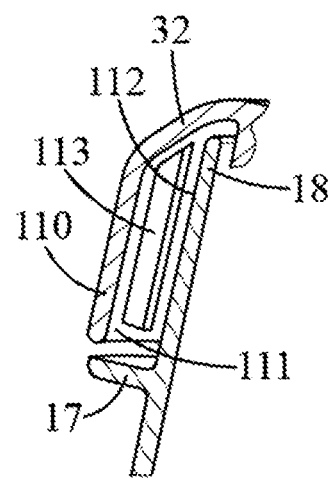
[Fig. 2]

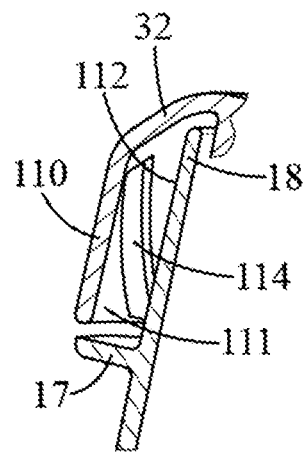
[Fig. 3]
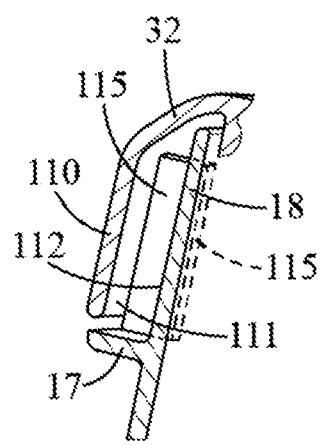
[Fig. 4]
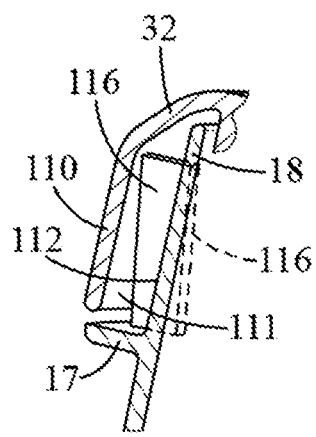
[Fig. 5]

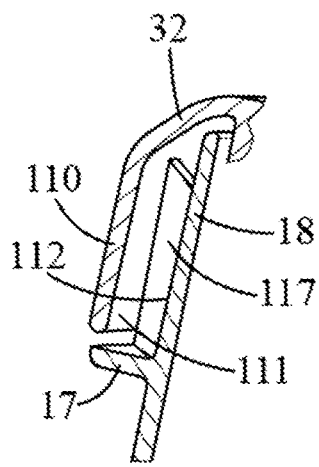
[Fig. 6]
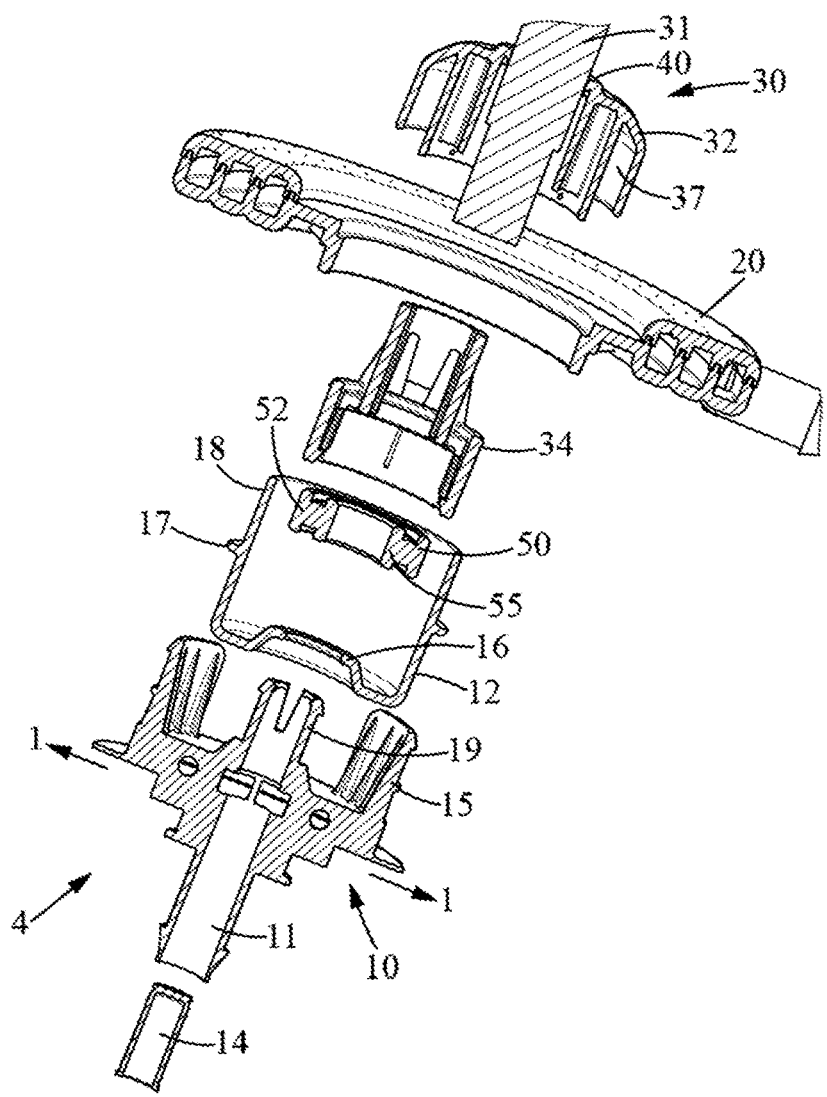
[Fig. 7]

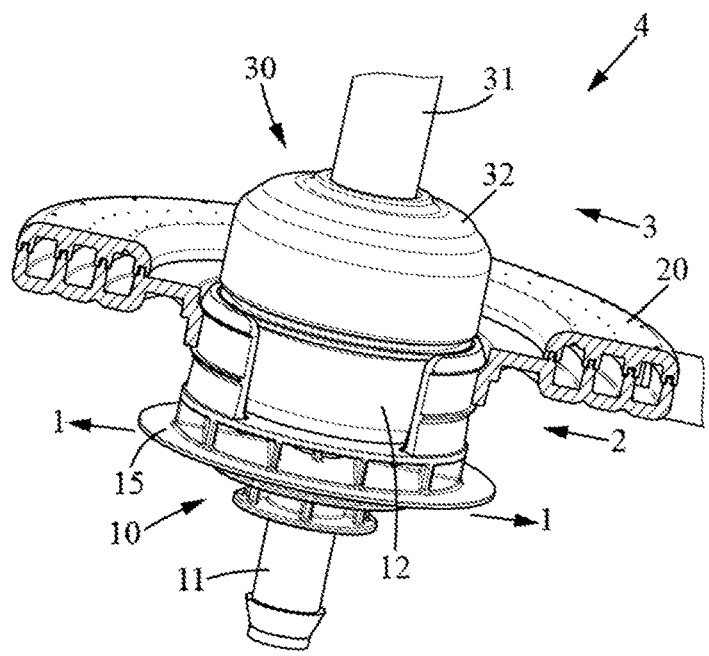
[Fig. 8]
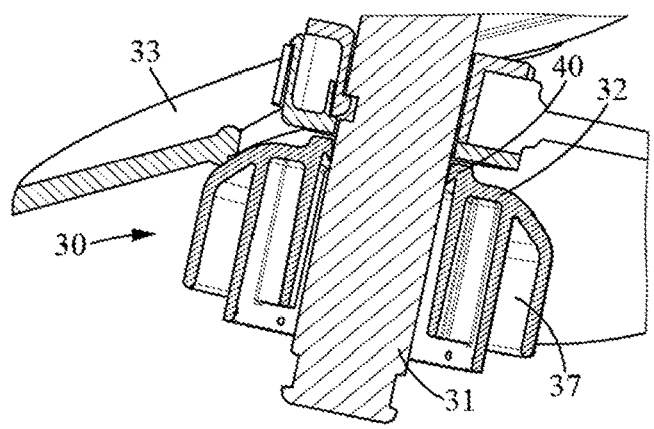
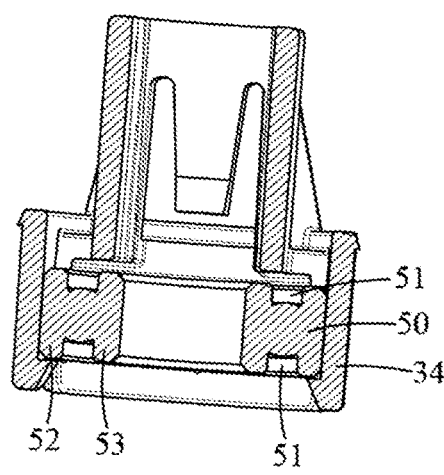
[Fig. 9]

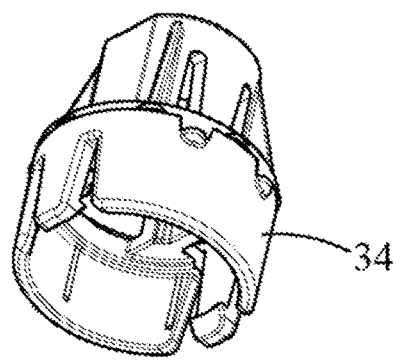
[Fig. 10]
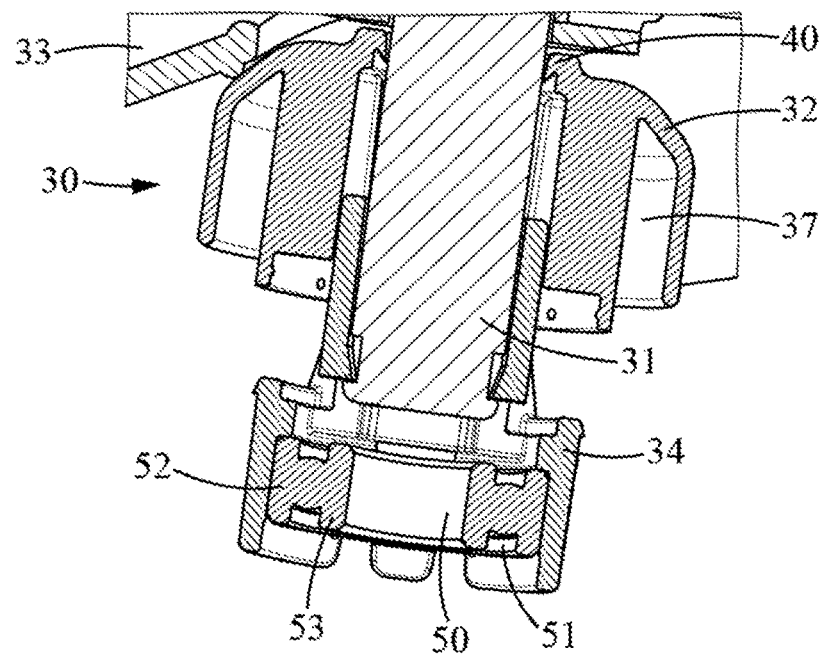
[Fig. 11]
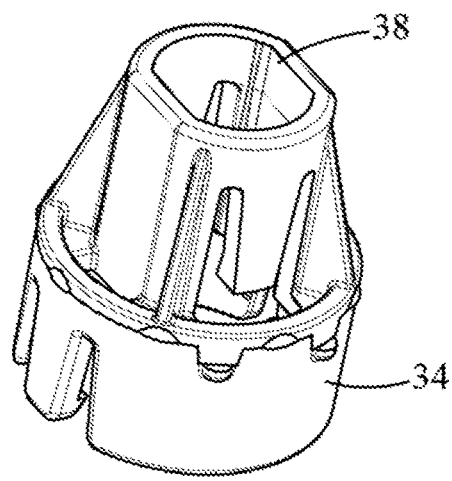
[Fig. 12]

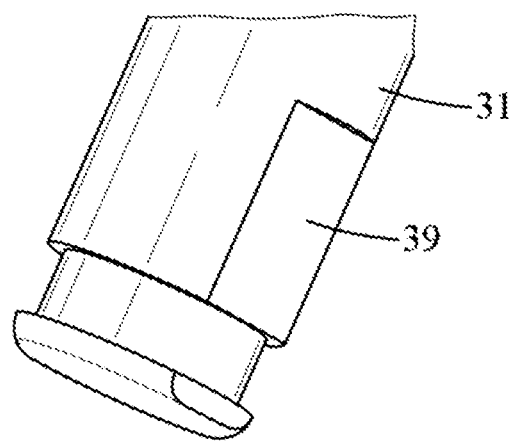
[Fig. 13]
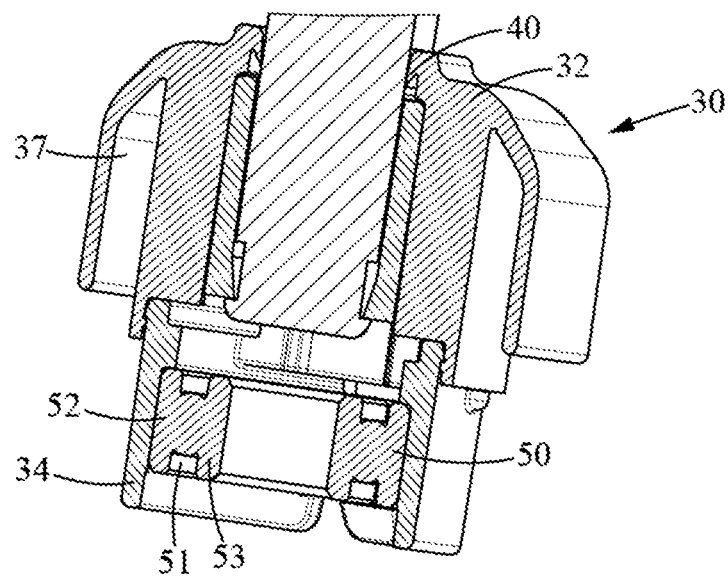
[Fig. 14]
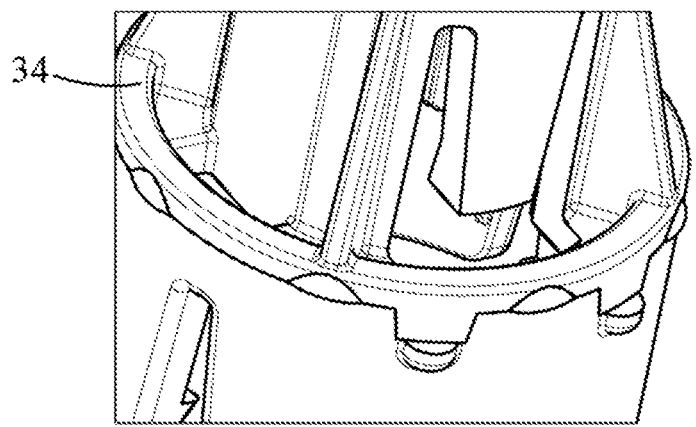
[Fig. 15]

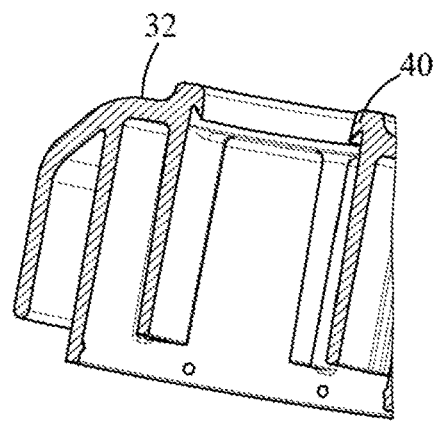
[Fig. 16]
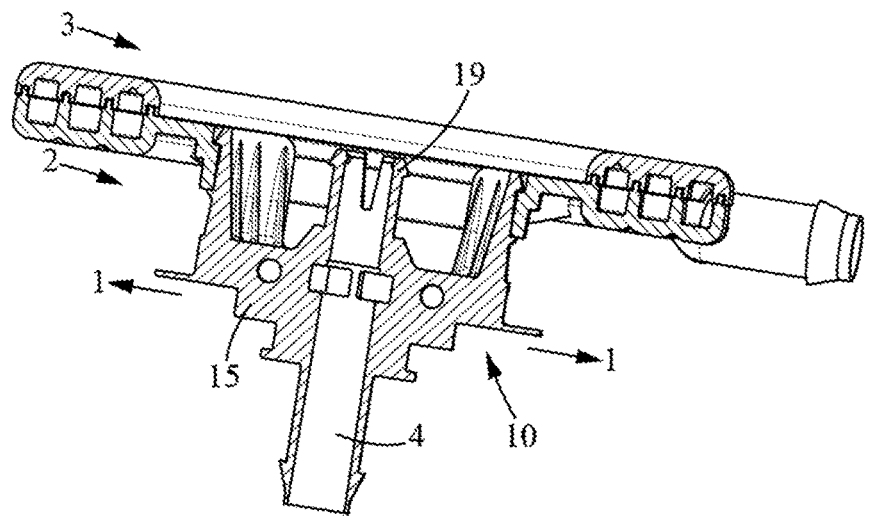
[Fig. 17]
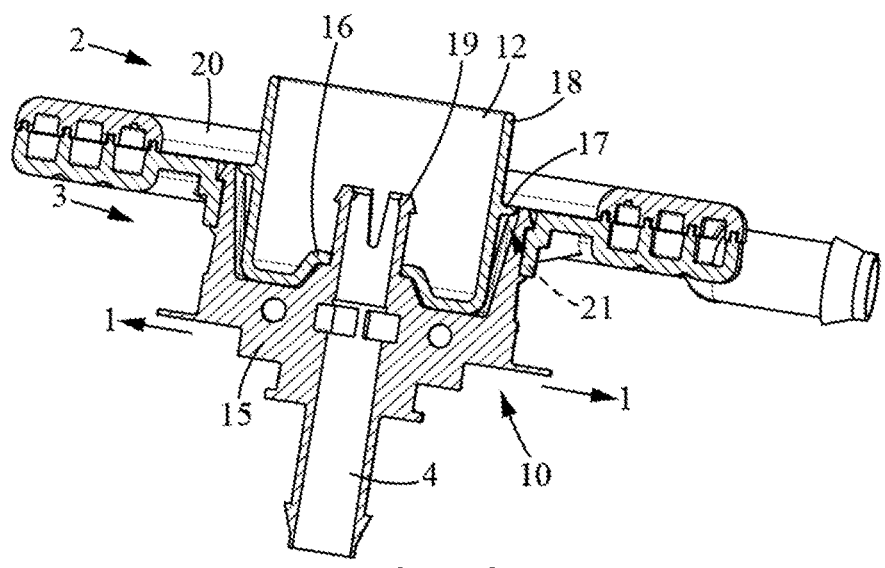
[Fig. 18]

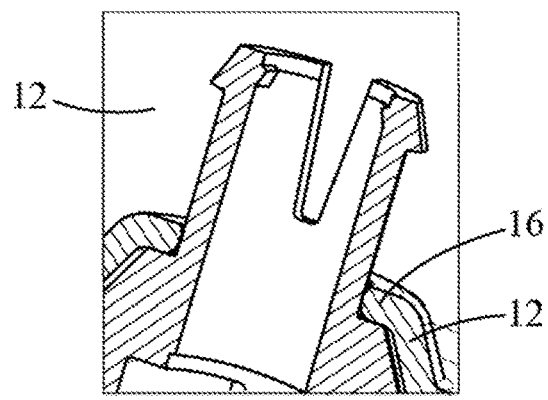
[Fig. 19]
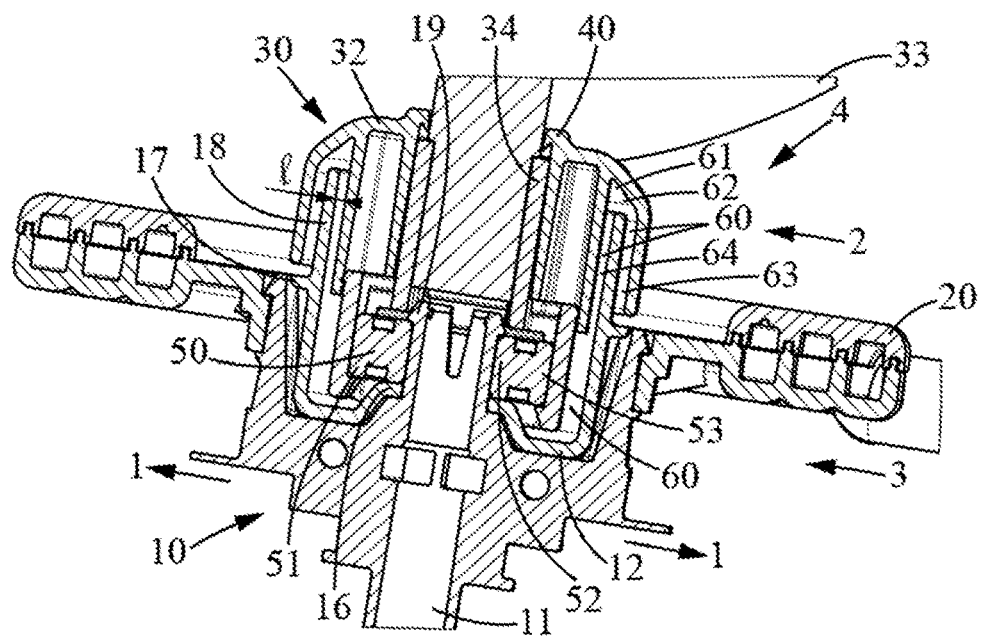
[Fig. 20]
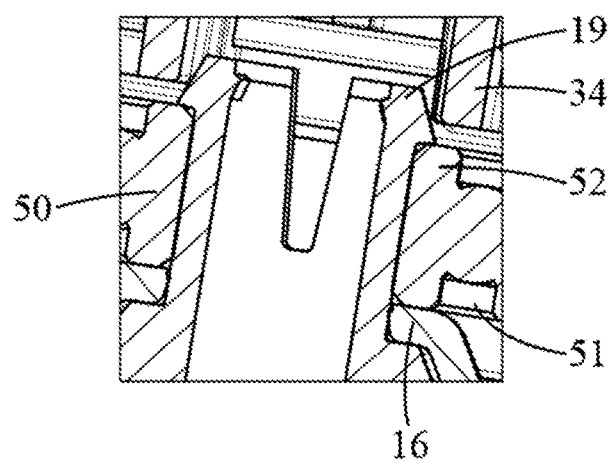
[Fig. 21]

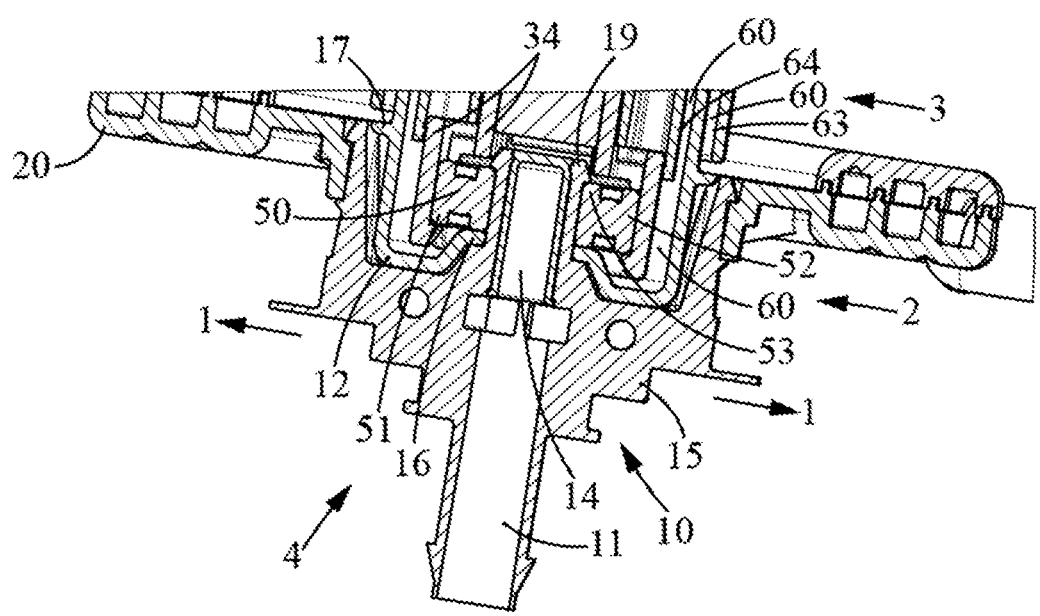
[Fig. 22]
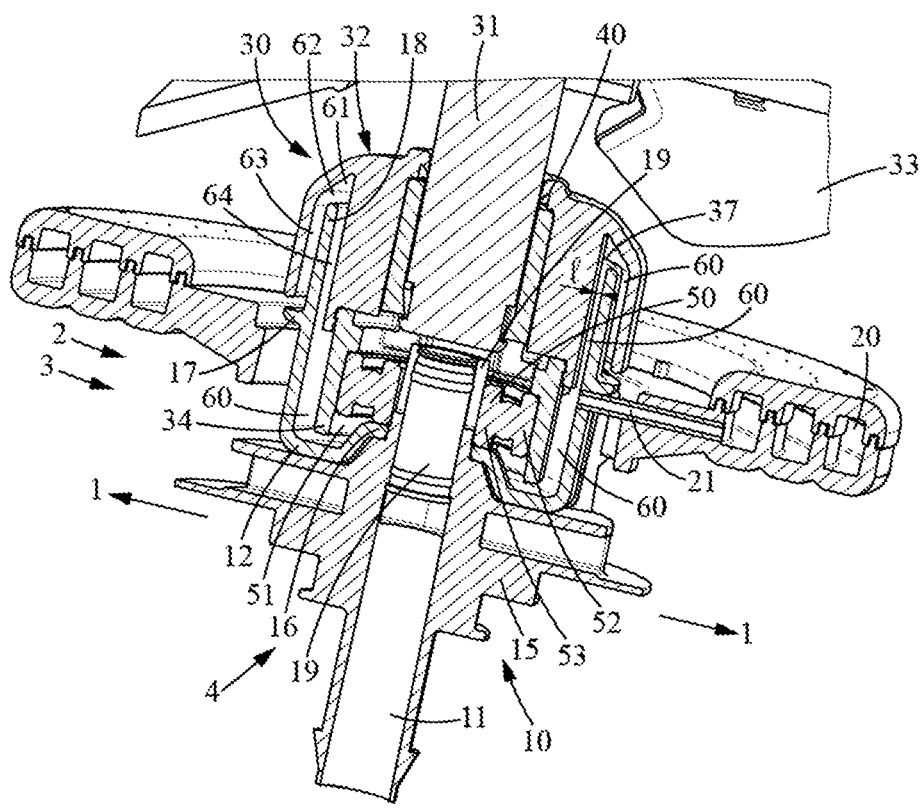
[Fig. 23]

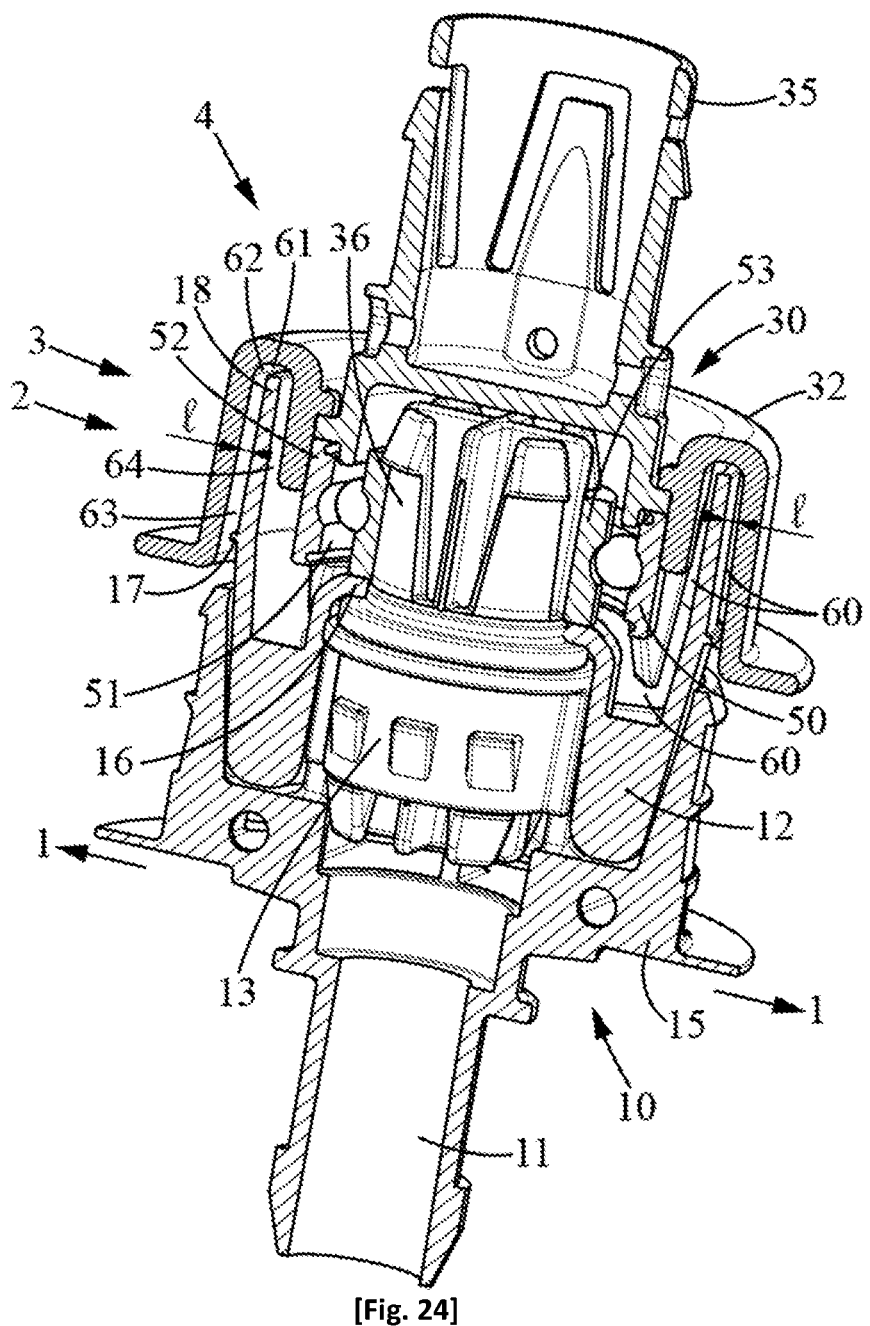
[Fig. 24]

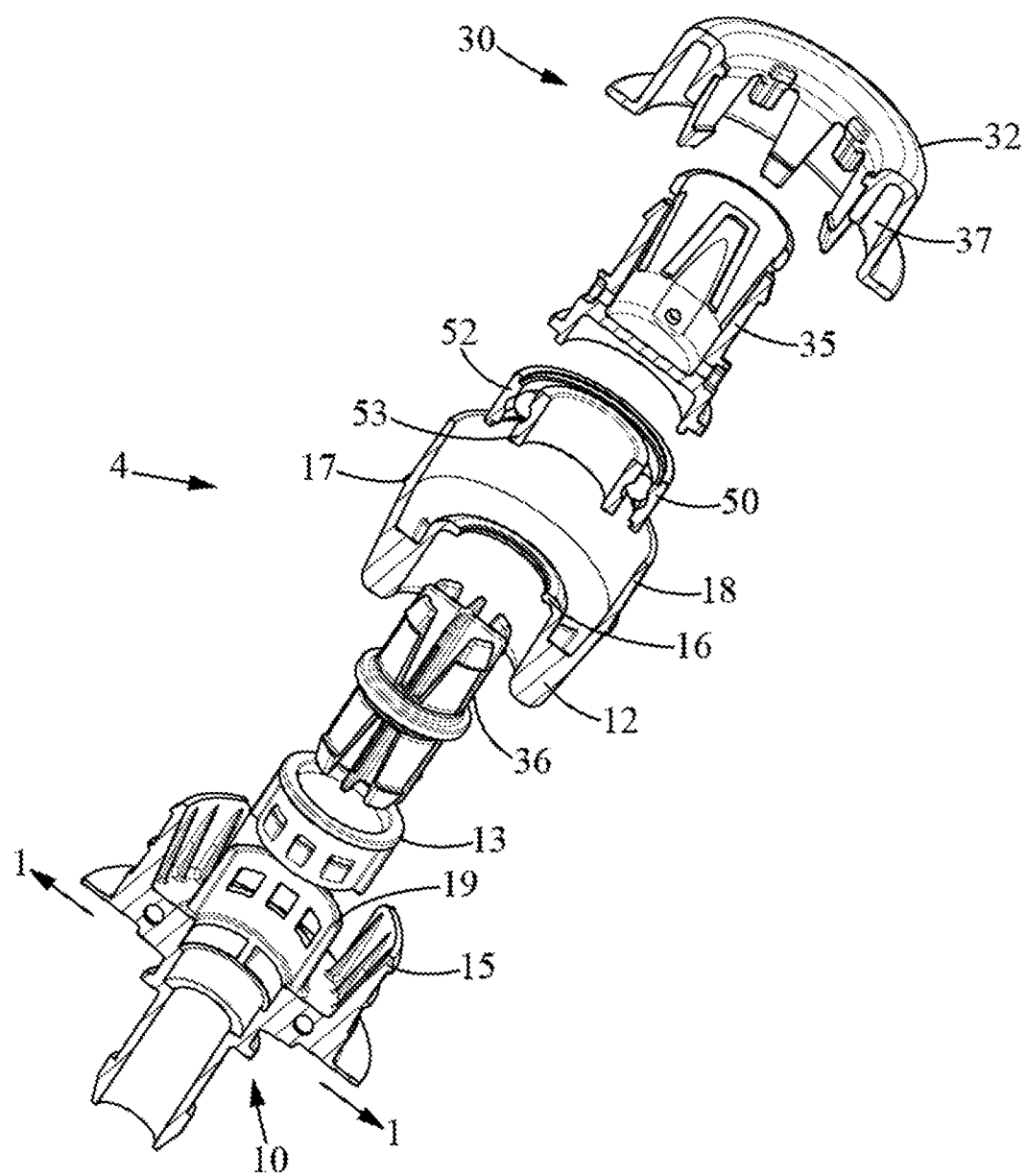
[Fig. 25]

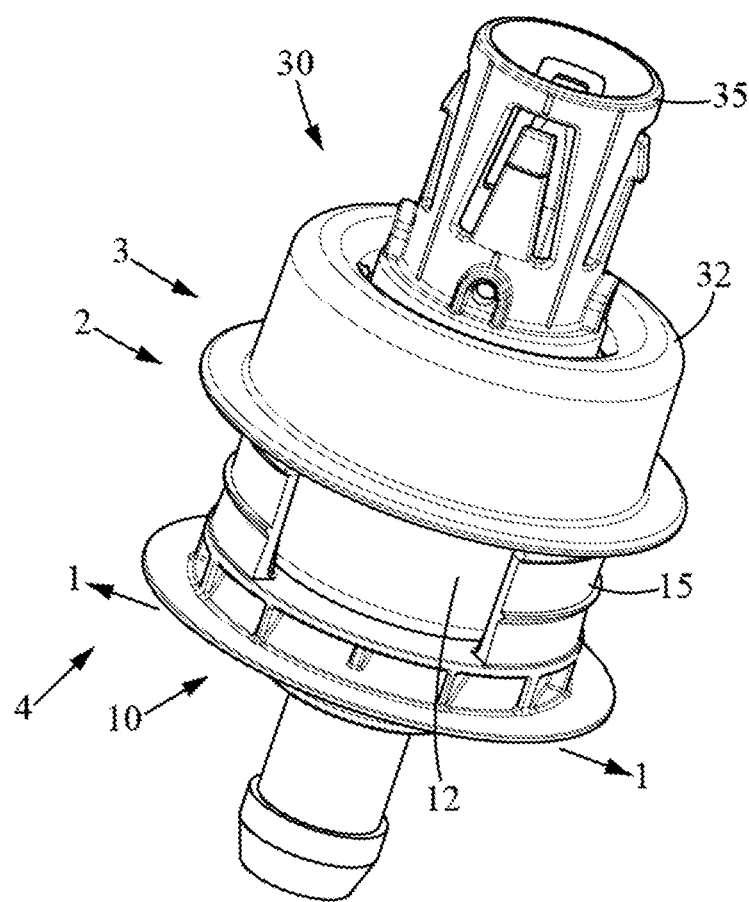
[Fig. 26]
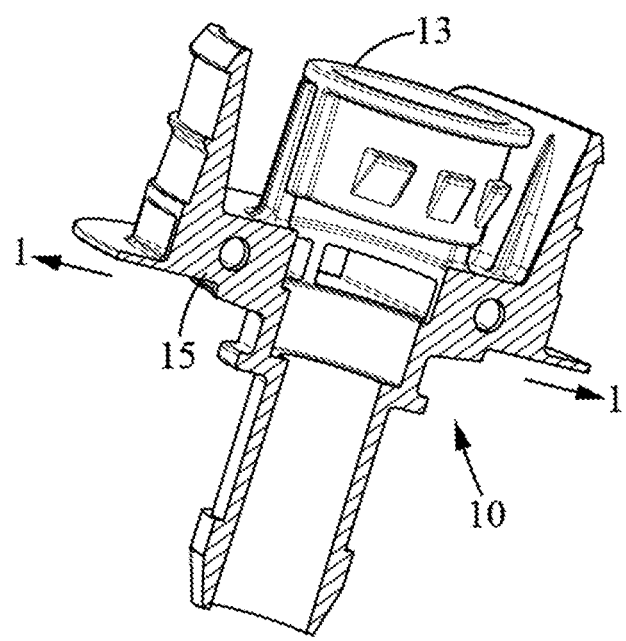
[Fig. 27]

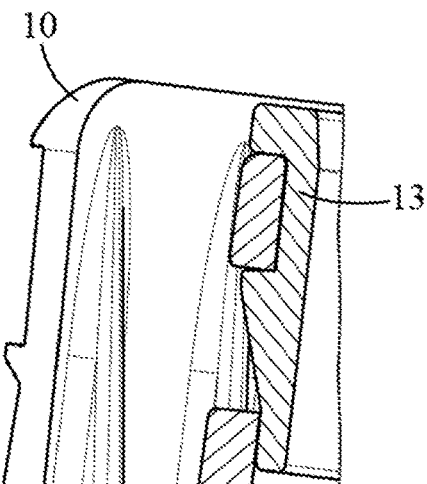
[Fig. 28]
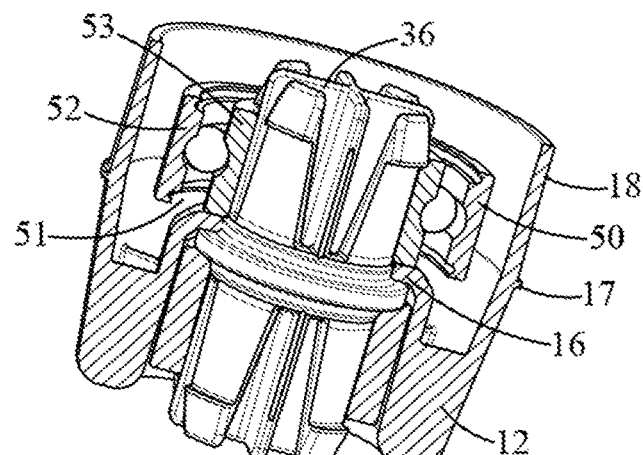
[Fig. 29]
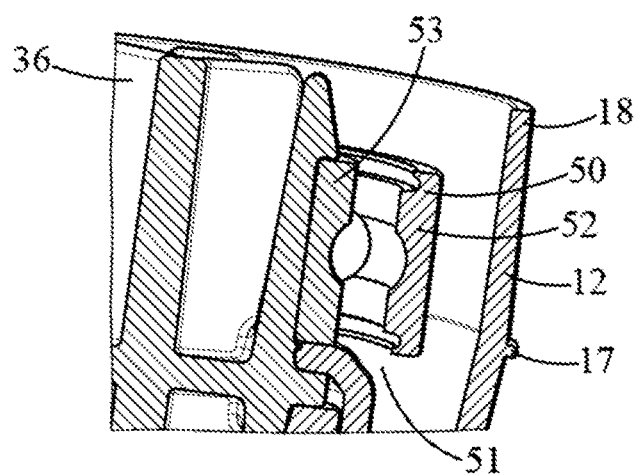
[Fig. 30]

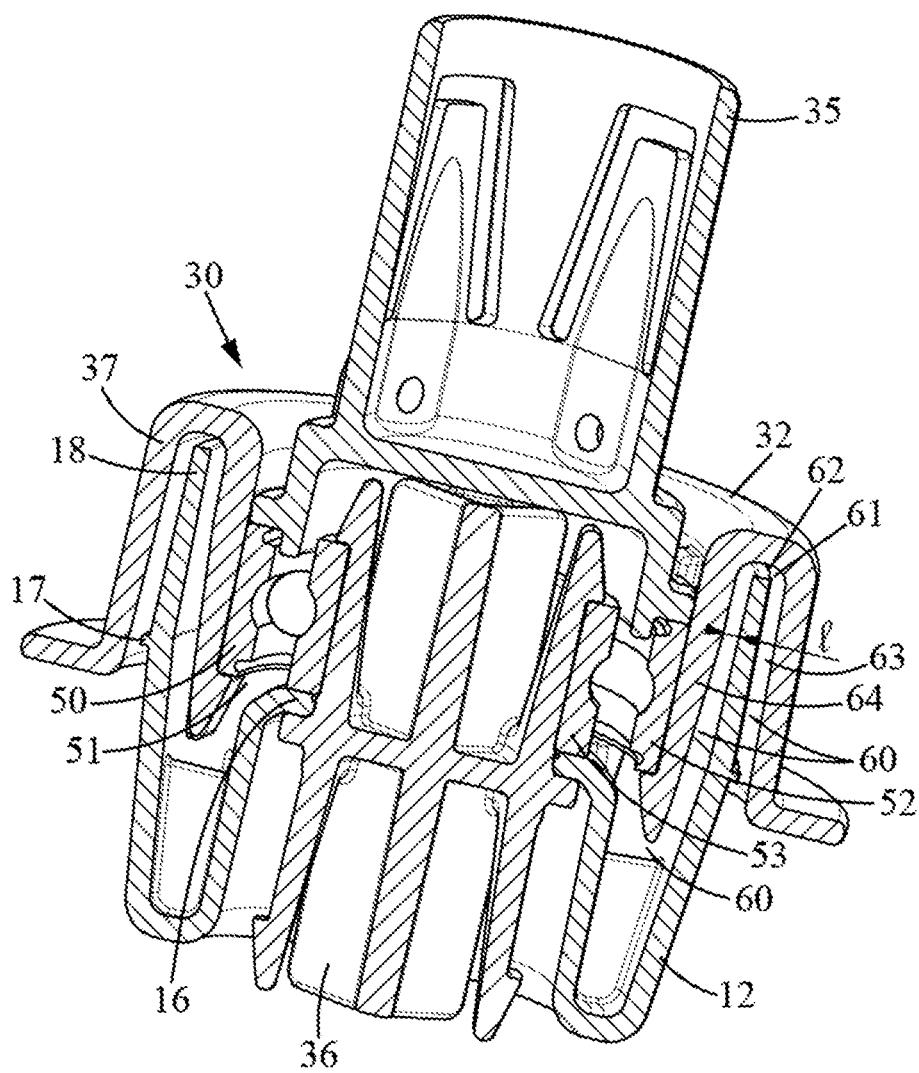
[Fig. 31]
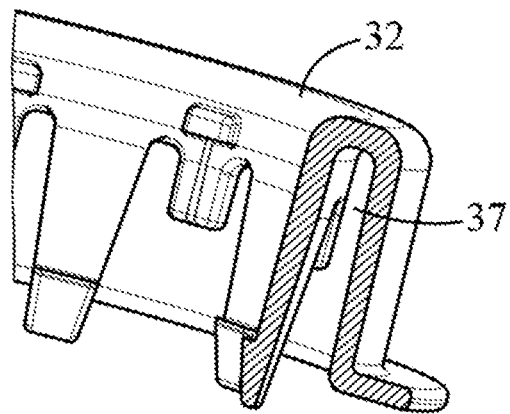
[Fig. 32]

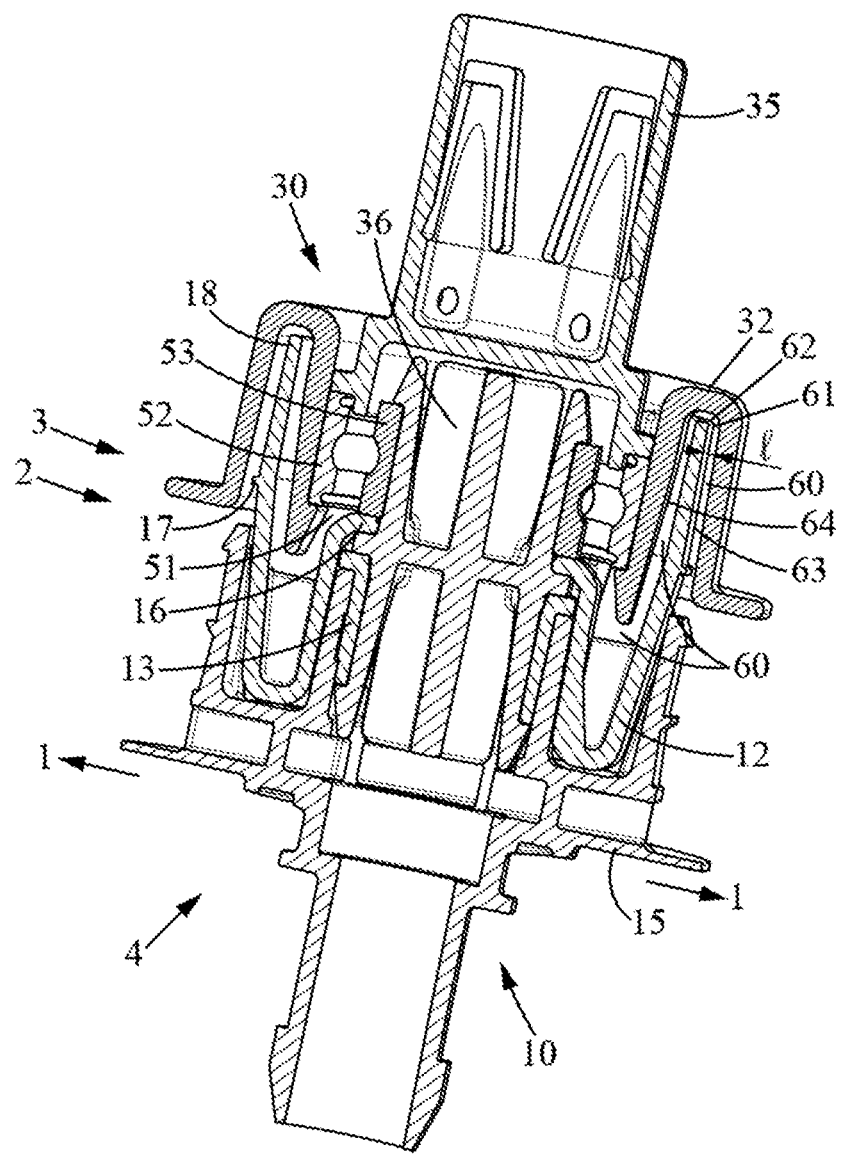
[Fig. 33]

BIOPHARMACEUTICAL LIQUID RESERVOIR WITH MECHANICAL MEMBER INCLUDING ROTATING AND STATIONARY SETS OF PARTS

CROSS REFERENCE TO RELATED APPLICATIONS

This application is a national stage filing under section 371 of International Application No. PCT/FR2019/000191, filed on Nov. 25, 2019, published on Jun. 11, 2020 as WO 2020/115372 A1 which claims priority to French Patent Application No. 1872448, filed on Dec. 6, 2018. The entire disclosure of each application is hereby incorporated herein by reference.

FIELD OF THE INVENTION

The invention relates to a biopharmaceutical liquid vessel, in particular intended for the mixing of biopharmaceutical products or more specifically to the cell culture comprising a bag, a stationary set of parts with respect to the bag, a rotating set of parts about an axis of rotation.

TECHNOLOGICAL BACKGROUND OF THE INVENTION

Vessels for stirring or mixing biopharmaceutical liquid use a, for example, rotating stirrer to mix between them, chemical compounds. Often, the components to be mixed require a sterile environment, as is the case for preparing a pharmaceutical product. To guarantee the sterility of the environment, the mixing vessels are structured so as to prevent external contaminating elements from entering into the vessel, and this all throughout the process, whether during filling, during mixing or also during draining the biopharmaceutical liquid.

According to a first prior art, there is a biopharmaceutical liquid vessel of which the substantial part of the mechanical member, and in particular the bearing of the rotating shaft, is located outside of the bag. A disadvantage of this first prior art is to require the passing through of the wall of the bag through the rotating shaft equipped with a rotating joint or a stationary friction joint. This rotating joint is complex, expensive and delicate. This stationary friction joint on the one hand is worn quickly, must therefore be replaced often, and on the other hand, creates a lot of particles which will pollute the biopharmaceutical liquid. One or the other of these joints imposes a limited rotation speed of the rotating shaft.

According to a second prior art, there is a biopharmaceutical liquid vessel of which the substantial part of the mechanical member, and in particular the bearing of the rotating shaft, is located inside the bag. A disadvantage of this second prior art is only separated from the inner storage space for storing biopharmaceutical liquid by a straight passage, moreover quickly fully filled with biopharmaceutical liquid, thus favoring on the one hand, the migration of the particles for wearing the bearing going to pollute the inner storage space for storing the biopharmaceutical liquid and on the other hand, the migration of cells and of the supports or micro-supports thereof being crushed in the bearing, risking damaging the bearing and polluting the inner storage space for storing the biopharmaceutical liquid with the debris crushed from the micro-supports then migrating in the other direction. Finally, the destruction of some of the cultivated cells damages the yield of the cell culture more.

AIMS OF THE INVENTION

The aim of the present invention is to provide a biopharmaceutical liquid vessel overcoming at least partially the abovementioned disadvantages.

More specifically, the invention aims to provide a biopharmaceutical liquid vessel which, on the one hand, localizes the substantially part of the mechanical member, and in particular, the bearing and the rotating member or element supported by this bearing, inside the bag, thus avoiding a delicate joint and a too limited rotation speed of the rotating member or element, and on the other hand, avoids or at least reduces notably the communication between, on the one hand, the surround of the bearing, source of wearing particles, and on the other hand, the inner storage space for storing biopharmaceutical liquid.

This suppression, or at least less reduction of communication, between the surround of the bearing and the inner storage space for storing biopharmaceutical liquid stored by the particles for wearing the bearing, and on the other hand, the crushing of the content of the biopharmaceutical liquid, cells and support elements, deteriorating the bearing and risking polluting the biopharmaceutical liquid stored during the return thereof into the inner storage space for storing this biopharmaceutical liquid in the bag of the vessel.

To this end, the present invention proposes a biopharmaceutical liquid vessel, comprising: a bag forming an inner storage space for storing biopharmaceutical liquid, a mechanical member located at a wall of the bag, comprising: a stationary set of parts, stationary with respect to the wall of the bag, a rotating set of parts, rotating about an axis of rotation with respect to the stationary set, a bearing located between the two sets and inside the bag, a communication passage: separating the bearing from the inner storage space, comprising one or more changes of direction, being formed by a portion of the parts of the rotating set located opposite a portion of the parts of the stationary set. In fact, this means that the communication passage is formed, on the one hand by a portion of the parts of the rotating set, and on the other hand, by a portion of the parts of the stationary set, said portion of the parts of the rotating set being located opposite said portion of the parts of the stationary set.

To this end, the invention also proposes a mechanical member for biopharmaceutical liquid vessel comprises a bag for storing the biopharmaceutical liquid, characterized in that it comprises: a stationary set of parts, a rotating set of part, rotating about an axis of rotation with respect to the stationary set, a bearing located between the two sets, a communication passage: separating the bearing from the outside of the mechanical member, comprising one or more changes of direction, being formed by a portion of the parts of the rotating set located opposite a portion of the parts of the stationary set.

According to preferred embodiments, the invention comprises one or more of the following features which can be used separately or in partial combination with one another or in total combination with one another.

Preferably, the passage forms an inverted siphon, for the air being trapped in the bottom of the inverted siphon by the liquid located at least in one branch of the inverted siphon starting at the bottom of the inverted siphon and opening into the inner storage space.

Thus, the presence of the siphon in the communication passage allows to reduce even further the communication, between the surround of the bearing and the inner storage space for storing biopharmaceutical liquid. The siphon is inverted, as it is the air trapped at the bottom of the siphon by the liquid in one and/or the other of the branches of the siphon extending on either side of the bottom of the siphon, instead of being the liquid trapped by the air like in a conventional sanitary discharge siphon.

Preferably, said air being trapped in the bottom of the inverted siphon by the liquid located at least in the two branches of the inverted siphon, the branch starting at the bottom of the inverted siphon and opening into the inner storage space and the branch starting at the bottom of the inverted siphon and going up to the bearing.

Thus, the air being trapped on each side by a liquid stopper, the communication between the surround of the bearing and the inner storage space for storing biopharmaceutical liquid is even further reduced, even can be practically removed.

Preferably, the communication passage mainly travels between two parts which are, on the one hand, a cap of the rotating set and a containment of the stationary set, the cap rotating about the axis of rotation with respect to the containment, the cap and the containment being interlocked at least partially one in the other to form the communication passage.

Thus, the space located between the rotating and stationary sets, low point of the vessel, is arranged so as to remove or at least reduce the communication possibility between the surround of the bearing and the inner storage space for storing biopharmaceutical liquid, the other spaces could more easily be made sealed, preferably by simple clipping of a part on another or of a part in another.

Preferably, one of the sets forms a projection entering into a cavity of the other set, the communication passage bypassing the projection by traveling along the walls of the cavity.

Thus, the communication between the surround of the bearing and the inner storage space for storing biopharmaceutical liquid is also reduced, and this in a simple manner. Indeed, a simple penetration of a male part in a female part allows to produce a chicane effectively reducing the communication between the surround of the bearing and the inner storage space for storing biopharmaceutical liquid.

Preferably, the rotating set forms the cavity, and the stationary set forms the projection.

Thus, the air is trapped more effectively, in the bottom of the siphon located higher than the branches of the siphon, the mechanical member thus being disposed in the bottom portion of the vessel, advantageously at the lower wall of the bag.

Preferably, the communication passage is a passage having a symmetry of revolution about the axis of rotation.

Thus, the bulk about the axis of rotation is minimized.

Preferably, the width of the communication passage in a plane containing the axis of rotation is comprised between 0.5 mm and 5 mm, preferably comprised between 1 mm and 3 mm.

Thus, the rotation of the rotating set, rotating about the stationary set is better secured, the space being wide enough to guarantee the absence of friction or fastening during the rotation, while reducing notably the communication between the surround of the bearing and the inner storage space for storing biopharmaceutical liquid, the space being also narrow enough to trap the air in the bottom of the siphon and to impede, even prevent the migration of undesirable elements from one of the sides to the other side, particles for wearing the bearing to the inner storage space, or cells and supports to the vicinity of the bearing.

Preferably, the communication passage comprises at least two passages parallel to the axis of rotation, separated by a bend.

Thus, the presence of this chicane reduces the communication between the surround of the bearing and the inner storage space for storing biopharmaceutical liquid.

Preferably, one of the passages parallel to the axis of rotation connects the bend to a cavity comprising the bearing.

Thus, this very simple and very short chicane, already sufficient, also reduces the risk of friction or fastening during the rotation of the rotating set, rotating about the stationary set, even after a significant time when these two sets already have wear marks due to the rotation.

Preferably, the communication passage comprises radial fins, advantageously regularly distributed about the axis of rotation, advantageously located in the branch of the inverted siphon starting at the bottom of the inverted siphon and opening into the inner storage space, advantageously 8 to 15 fins. Advantageously, these radial fins only extend over a portion of the width of the communication passage.

Thus, the presence of these radial fins allows to better trap possible solid particles which would be located in the communication passage forming inverted siphon, or to prevent or to impede such solid particles which would tend to enter into the communication passage forming inverted siphon or also to pass through it.

Preferably, the radial fins extend, advantageously perpendicularly, from the outer face of the inner wall of a portion of the stationary set.

Thus, the presence of these radial fins disrupts the hydrodynamics of the liquid located in the communication passage forming inverted siphon less. Alternatively, the radial fins can extend, advantageously perpendicularly, from the inner face of the outer face of a portion of the rotating set.

Preferably, the radial fins extend in an inclined manner, with respect to a wall inside the communication passage, the direction of the inclination being such that given the direction of rotation of the rotating set rotating about the stationary set of possible solid particles located in the communication passage remain retained or blocked between the fins and said wall inside the communication passage.

Alternatively, the radial fins can extend in a straight manner with respect to a wall inside the communication passage forming inverted siphon.

In variants:

- these fins can be flat plates parallel to the axis of rotation,
- these fins can be curved and inclined plates, mainly with respect to the axis of rotation with an acute angle, preferably less than 30 degrees, advantageously of the order of 15 degrees,
- these fins can be straight plates inclined with respect to the axis of rotation with an acute angle, preferably less than 30 degrees, advantageously of the order of 15 degrees.

Preferably, the bearing is the only zone for supporting the rotating set with the stationary set.

Thus, the reduction of the communication between the surround of the bearing and the inner storage space for storing biopharmaceutical liquid is therefore particularly critical there.

Preferably, the bearing is the only contact zone between the rotating set and the stationary set.

Thus, the reduction of the communication between the surround of the bearing and the inner storage space for storing biopharmaceutical liquid is therefore particularly critical there.

Preferably, the bearing is a ball bearing.

Thus, the reduction of the communication between the surround of the bearing and the inner storage space for storing biopharmaceutical liquid is particularly interesting, as the ball bearing is particularly capable of crushing into small pieces all the small elements, like the cells of the biopharmaceutical liquid or the supports thereof, these small pieces being particularly capable of returning to pollute the biopharmaceutical liquid stored and being particularly difficult to filter during a subsequent partial or total draining of the bag, once the cells are sufficiently multiplied in the biopharmaceutical liquid stored in the inner storage space of the bag.

Preferably, the mechanical member passes through the wall of the bag at an opening of the wall of the bag.

Thus, the holding of the bearing inside the bag is particularly advantageous, as it avoids any complex and delicate joint, like a rotating joint, present in the first prior art.

Preferably, the opening of the wall of the bag is fixed in a sealed manner around the mechanical member.

Thus, any direct leakage of the biopharmaceutical liquid stored in the bag towards the outside of the bag just like any pollution of this biopharmaceutical liquid stored by the particles directly coming from the outside of the bag, can be avoided.

Preferably, the opening is welded or glued about the stationary set.

Thus, this sealing between the bag and the outside of the bag, at the mechanical member, is done simply.

Preferably, the rotating set carries a rotating shaft.

Thus, a rotating shaft requiring a relatively high rotation speed of the rotating set, rotating about the stationary set, it is particularly interesting to reduce the communication between the surround of the bearing and the inner storage space for storing biopharmaceutical liquid.

Preferably, the rotating shaft itself carries a propeller.

Thus, this propeller leading to increased pollution risks due to the significant driven vibrations, it is particularly interesting to reduce the communication between the surround of the bearing and the inner storage space for storing biopharmaceutical liquid.

Preferably, the stationary set comprises a draining port opening to the outside of the bag.

Thus, the sealing of the mechanical member at the wall of the bag is all the more important to maintain.

Preferably, a gas distributor is located around the sets, in the inner storage space.

Thus, this gas distributor leading to an increase of the circulation of the biopharmaceutical liquid in the vicinity of the mechanical member, it is all the more important to reduce the communication between the surround of the bearing and the inner storage space for storing biopharmaceutical liquid.

Preferably, the gas distributor is annular.

Thus, the increase of the circulation of the biopharmaceutical liquid in the vicinity of the mechanical member is even done all around the mechanical member, it is thus all the more important to reduce the communication between the surround of the bearing and the inner storage space for storing biopharmaceutical liquid.

Preferably, the gas distributor comprises a diversion capable of blowing air into the communication passage so as to tend to make it emerge in the inner storage space.

Thus, this diversion will help improve the reduction of the communication between the surround of the bearing and the inner storage space for storing biopharmaceutical liquid, by repelling the biopharmaceutical liquid into the inner storage space from where it comes.

Preferably, the rotating set comprises an intermediate connecting part carrying the rotating shaft and the bearing.

Thus, the presence of this intermediate connecting part allows more easily to arrange the surround of the bearing so as to then be able to reduce the communication more easily between the surround of the bearing and the inner storage space for storing biopharmaceutical liquid.

Preferably, the rotating shaft is clipped in the intermediate connecting part.

Thus, the sealing at this place is more easily achieved both simply and effectively.

Preferably, the bearing comprises a rotating ring, preferably the outer ring of the bearing, which is clipped in the intermediate connecting part.

Thus, the sealing at this place is more easily achieved both simply and effectively.

Preferably, the intermediate connecting part carries the rotating cap which is clipped on this intermediate connecting part.

Thus, the sealing at this place is more easily achieved both simply and effectively.

Preferably, the stationary set comprises a base which carries the bearing, and which has a draining port opening to the outside of the inner storage space.

Thus, it is particularly interesting to guarantee the sealing between the inside and the outside of the bag at the mechanical member.

Preferably, the gas distributor is clipped around the base.

Thus, the sealing at this place is more easily achieved both simply and effectively.

Preferably, the bearing is clipped around the base.

Thus, the sealing at this place is more easily achieved both simply and effectively.

Preferably, the bearing comprises a stationary ring, which is preferably the inner ring of the bearing, which holds the containment blocked against the base.

Thus, the sealing at this place is more easily achieved both simply and effectively.

Preferably, the biopharmaceutical liquid comprises: inert micro-supports, of which the largest dimension is less than 0.3 mm, preferably less than 0.1 mm, advantageously greater than 10 μm, cells fastened to these micro-supports.

Thus, it is particularly interesting to reduce the communication between the surround of the bearing and the inner storage space for storing biopharmaceutical liquid, since the very low size of the solid elements of the biopharmaceutical liquid stored makes them particularly capable of being moved everywhere, and in particular to slide into the bearing if they could do so.

Preferably, the micro-supports are balls.

Thus, these spherical elements of the biopharmaceutical liquid stored are moved even more easily, and even in confined places; hence the interest in also reducing the communication between the surround of the bearing and the inner storage space for storing biopharmaceutical liquid.

Preferably, most of the parts of the sets are made of rigid plastic, slightly deformable so as to be able to carry out an operation of clipping together, are preferably made of polyethylene (PE).

Thus, the sealing at this place is more easily achieved both simply and effectively, while easily allowing the mechanical member to fulfill the mechanical function thereof, here in particular a rotating mechanical function requiring a certain rigidity of the constituting parts thereof Preferably, the wall of the bag is made of sufficiently flexible and deformable material to be able to be folded.

Thus, the sealing at a wall, and in particular at an opening in the wall, is all the more interesting to achieve.

A bearing is a mechanical member supporting and guiding a rotating mechanical member, preferably a rotating shaft.

A clip is a fastening system integrated or not to the part, which is elastically deformed during the insertion thereof, and which after insertion, generally no longer undergoes any stress.

A clipping is an assembly operation wherein the elastic deformation of one of two parts involved during the insertion phase allows the attachment thereof after elastic return. The clipping achieves an interlocking of parts using the elastic deformation of certain elements, for example of a female part, often made of plastic material, and advantageously comprises one or more claws (one or more lugs) of which the shape can allow an easy and quick disassembly.

Other features and advantages of the invention will appear upon reading the following description of a preferred embodiment of the invention, given as an example and in reference to the appended drawings.

BRIEF DESCRIPTION OF THE DRAWINGS

FIG. 1 schematically represents an overall perspective, cross-sectional view of an example of assembly of stationary and rotating sets of the mechanical member of the biopharmaceutical liquid vessel according to a first embodiment of the invention.

FIG. 2 schematically represents an overall perspective, cross-sectional view of an optional detail showing the fins in the communication passage, of an example of assembly of stationary and rotating sets of the mechanical member of the biopharmaceutical liquid vessel according to a first embodiment of the invention.

FIG. 3 schematically represents an overall perspective, cross-sectional view of an optional detail showing the fins in the communication passage, of an example of assembly of stationary and rotating sets of the mechanical member of the biopharmaceutical liquid vessel according to a first embodiment of the invention.

FIG. 4 schematically represents an overall perspective, cross-sectional view of an optional detail showing the fins in the communication passage, of an example of assembly of stationary and rotating sets of the mechanical member of the biopharmaceutical liquid vessel according to a first embodiment of the invention.

FIG. 5 schematically represents an overall perspective, cross-sectional view of an optional detail showing the fins in the communication passage, of an example of assembly of stationary and rotating sets of the mechanical member of the biopharmaceutical liquid vessel according to a first embodiment of the invention.

FIG. 6 schematically represents an overall perspective, cross-sectional view of an optional detail showing the fins in the communication passage, of an example of assembly of stationary and rotating sets of the mechanical member of the biopharmaceutical liquid vessel according to a first embodiment of the invention.

FIG. 7 schematically represents an overall exploded perspective view of an example of assembly of stationary and rotating sets of the mechanical member of the biopharmaceutical liquid vessel according to a first embodiment of the invention.

FIG. 8 schematically represents an overall perspective view of an example of assembly of stationary and rotating sets of the mechanical member of the biopharmaceutical liquid vessel according to a first embodiment of the invention.

FIG. 9 schematically represents an overall perspective, cross-sectional view of an example of a rotating set of the mechanical member of the biopharmaceutical liquid vessel according to a first embodiment of the invention.

FIG. 10 schematically represents a local perspective view of an example of a portion of a rotating set of the mechanical member of the biopharmaceutical liquid vessel according to a first embodiment of the invention.

FIG. 11 schematically represents an overall perspective, cross-sectional view of an example of a rotating set of the mechanical member of the biopharmaceutical liquid vessel according to a first embodiment of the invention.

FIG. 12 schematically represents a local perspective view of an example of a portion of a rotating set of the mechanical member of the biopharmaceutical liquid vessel according to a first embodiment of the invention.

FIG. 13 schematically represents a local perspective view of an example of a portion of a rotating set of the mechanical member of the biopharmaceutical liquid vessel according to a first embodiment of the invention.

FIG. 14 schematically represents an overall perspective, cross-sectional view of an example of a rotating set of the mechanical member of the biopharmaceutical liquid vessel according to a first embodiment of the invention.

FIG. 15 schematically represents a local perspective view of an example of a portion of a rotating set of the mechanical member of the biopharmaceutical liquid vessel according to a first embodiment of the invention.

FIG. 16 schematically represents a local perspective view of an example of a portion of a rotating set of the mechanical member of the biopharmaceutical liquid vessel according to a first embodiment of the invention.

FIG. 17 schematically represents an overall perspective, cross-sectional view of an example of a stationary set of the mechanical member of the biopharmaceutical liquid vessel according to a first embodiment of the invention.

FIG. 18 schematically represents an overall perspective, cross-sectional view of an example of a stationary set of the mechanical member of the biopharmaceutical liquid vessel according to a first embodiment of the invention.

FIG. 19 schematically represents a local perspective, cross-sectional view of an example of a portion of a stationary set of the mechanical member of the biopharmaceutical liquid vessel according to a first embodiment of the invention.

FIG. 20 schematically represents an overall perspective, cross-sectional view of an example of a stationary set of the mechanical member of the biopharmaceutical liquid vessel according to a first embodiment of the invention.

FIG. 21 schematically represents a local perspective, cross-sectional view of an example of a portion of a stationary set of the mechanical member of the biopharmaceutical liquid vessel according to a first embodiment of the invention.

FIG. 22 schematically represents an overall perspective, cross-sectional view of an example of a stationary set of the mechanical member of the biopharmaceutical liquid vessel according to a first embodiment of the invention.

FIG. 23 schematically represents an overall perspective, cross-sectional view of an example of assembly of stationary and rotating sets of the mechanical member of the biopharmaceutical liquid vessel according to a first embodiment of the invention, showing the diversion connecting the gas distributor and the communication passage.

FIG. 24 schematically represents an overall perspective, cross-sectional view of an example of assembly of stationary and rotating sets of the mechanical member of the biopharmaceutical liquid vessel according to a second embodiment of the invention.

FIG. 25 schematically represents an overall exploded perspective, cross-sectional view of an example of assembly of stationary and rotating sets of the mechanical member of the biopharmaceutical liquid vessel according to a second embodiment of the invention.

FIG. 26 schematically represents an overall perspective view of an example of assembly of stationary and rotating sets of the mechanical member of the biopharmaceutical liquid vessel according to a second embodiment of the invention.

FIG. 27 schematically represents an overall perspective, cross-sectional view of an example of a stationary set of the mechanical member of the biopharmaceutical liquid vessel according to a second embodiment of the invention.

FIG. 28 schematically represents a local perspective, cross-sectional view of an example of a portion of a stationary set of the mechanical member of the biopharmaceutical liquid vessel according to a second embodiment of the invention.

FIG. 29 schematically represents an overall perspective, cross-sectional view of an example of a rotating set of the mechanical member of the biopharmaceutical liquid vessel according to a second embodiment of the invention.

FIG. 30 schematically represents a local perspective, cross-sectional view of an example of a portion of a rotating set of the mechanical member of the biopharmaceutical liquid vessel according to a second embodiment of the invention.

FIG. 31 schematically represents an overall perspective, cross-sectional view of an example of a rotating set of the mechanical member of the biopharmaceutical liquid vessel according to a second embodiment of the invention.

FIG. 32 schematically represents a local perspective, cross-sectional view of an example of a portion of a rotating set of the mechanical member of the biopharmaceutical liquid vessel according to a second embodiment of the invention.

FIG. 33 schematically represents an overall perspective, cross-sectional view of an example of a stationary set of the mechanical member of the biopharmaceutical liquid vessel according to a second embodiment of the invention.

DESCRIPTION OF PREFERRED EMBODIMENTS OF THE INVENTION

FIGS. 1 to 22 represent a first embodiment of the invention, corresponding advantageously to a bag volume comprised between 50 and 200 liters.

FIGS. 23 to 33 represent a second embodiment of the invention, corresponding advantageously to a bag volume comprised between 500 and 1000 liters.

FIG. 1 schematically represents an overall perspective, cross-sectional view of an example of assembly of stationary and rotating sets of the mechanical member of the biopharmaceutical liquid vessel according to a first embodiment of the invention.

The biopharmaceutical liquid vessel comprises a bag 1 and a mechanical member 4. The mechanical member 4 is fastened to an opening in the wall of the bag 1 which is not represented in FIG. 1 but extends around the mechanical member 4 in the directions of the arrows 1. The bag 1 forms an inner storage space 2 for storing a biopharmaceutical liquid 3. The mechanical member 4 passes through the wall of the bag 1.

The mechanical member 4 comprises a stationary set 10 of parts, stationary with respect to the wall of the bag 1, and a rotating set 30 of parts, rotating about an axis of rotation 31 with respect to the stationary set 10. A bearing 50 is located, on the one hand, between the two sets 10 and 30 and, on the other hand, inside 2 the bag 1.

A communication passage 60 separates the bearing 50 from the inner storage space 2. This communication passage 60 comprises one or more changes of direction, for example here from the outside to the inside, this communication passage 60 starts at the small projection 17 with a small horizontal passage to the inside, then with a quite large ascending passage, then with a small horizontal passage to the inside (in fact, it is a bend), then with a quite large descending passage, and finally with a small horizontal passage to the inside, before arriving in the cavity 51 where the bearing 50 is located. This communication passage 60 is formed by a portion of the parts of the rotating set 30, located opposite a portion of the parts of the stationary set 10.

This passage 60 forms an inverted siphon 61, the air being trapped in the bottom 62 of the inverted siphon 61 by the liquid located at least in one branch 63 of the inverted siphon 61 starting at the bottom 62 of the inverted siphon 61 and opening into the inner storage space 2. The air is trapped in the bottom 62 of the inverted siphon 61 by the liquid, preferably located at least in the two branches 63 and 64 of the inverted siphon 61, the branch 63 starting at the bottom 62 of the inverted siphon 61 and opening into the inner storage space 2 and the branch 64 starting at the bottom 62 of the inverted siphon 61 and going up to the bearing 50. This inverted siphon 61, of which the bottom 62 contains air and of which the branches 63 and 64 contain liquid, possibly the biopharmaceutical liquid 3, allows to block the passage of this biopharmaceutical liquid, on the one hand from the branch 63 to the branch 64, and on the other hand from the branch 64 to the branch 63.

This communication passage 60 mainly travels between two parts which are, on the one hand, a cap 32 of the rotating set 30 and a containment 12 of the stationary set 10, the cap 32 rotating about the axis of rotation 31 with respect to the containment 12, the cap 32 and the containment 12 being interlocked at least partially one in the other to form the communication passage 60. One of the sets 10 forms a projection 18 entering into a cavity 37 of the other set 30, the communication passage 60 bypassing the projection 18 by traveling along the walls of the cavity 37. Preferably, the rotating set 30 forms the cavity 37 and the stationary set 10 forms the projection 18.

The communication passage 60 is a passage having a symmetry of revolution about the axis of rotation 31. The width l of the communication passage 60 in a plane (for example, the plane of FIG. 1) containing the axis of rotation 31 is comprised between 0.5 mm and 5 mm, preferably comprised between 1 mm and 3 mm. The communication passage 60 comprises at last two passages parallel 63 and 64 to the axis of rotation 31, separated by a bend 62. One of the passages 64 parallel to the axis of rotation 31 connects the bend 62 to a cavity 51 comprising the bearing 50. The bearing 50 is the only support zone of the rotating set 30 by the stationary set 10. The bearing 50 is even the only contact zone between the rotating set 30 and the stationary set 10. Advantageously, the bearing is a ball bearing.

The mechanical member 4 passes through the wall of the bag 1 at an opening of the wall of the bag 1, which bag 1 therefore extends around the mechanical member 4 in the directions of the arrows 1. The opening of the wall of the bag 1 (not represented in FIG. 1, but of which the placement is marked by the extension of the arrows 1) is fastened in a sealed manner around the mechanical member 4. This opening is welded or glued around the stationary set 10. The rotating set 30 carries a rotating shaft 31. The rotating shaft 31 itself carries a propeller 33. The propeller 33 can, for example, rotate between 10 and 500 rotations per minute, for example at 50 rotations per minute for a bag 1 of 2000 liters of biopharmaceutical liquid 3 and, for example, at 250 rotations per minute for a bag 1 of 50 liters of biopharmaceutical liquid 3. The biopharmaceutical liquid 3 is advantageously a cultivated cell medium, also called "cell culture", which will require a quite strong stirring to be developed, leading to a relatively high rotation speed of the rotating shaft 31, which makes the isolation system by inverted siphon 61 between the cavity 51 of the bearing 50 on the one hand and the inner storage space 2 for storing biopharmaceutical liquid 3 on the other hand, proposed by the all-the-more interesting invention.

A gas distributor 20 is located around the sets and 10 and 30, in the inner storage space 2. This gas distributor 20 is annular. This gas distributor 20 comprises a diversion 21 capable of blowing air into the communication passage 60 so as to tend to make it emerge into the inner storage space 2, which contributes to also repelling the biopharmaceutical liquid 3 a little more, trying to pass through the inner storage space 2 to the branch 63 of the inverted siphon 61.

The rotating set 30 comprises an intermediate connecting part 34 carrying the rotating shaft 31 and the bearing 50. The rotating shaft 31 is clipped in the intermediate connecting part 34. The bearing 50 comprises a rotating ring 52, preferably the outer ring 52 of the bearing 50, which is clipped in the intermediate connecting part 34. The intermediate connecting part 34 carries the rotating cap 32 which is clipped on this intermediate connecting part 34.

The stationary set 10 comprises a base 15 which carries the bearing 50 and which has a draining port 11 opening to the outside of the inner storage space 2. This draining port 11 serves as the partial draining of the bag 1. This draining port 11 opens to the outside of the bag 1. It is through this draining port 11 that the fastening part 14 of the rotating set 30 is introduced with respect to the stationary set 10. This fastening part 14 is press-fitted into the stationary set 10 by deviating the walls of the central funnel 19 which itself pushes on the bearing 50, thus relatively fastening the rotating 30 and stationary 10 sets against one another. It is this fastening part 14 which maintains the assembly of the rotating set 30 on the stationary set 10. The gas distributor 20 is clipped around the base 15. The bearing 50 is clipped around the base 15. The bearing 50 comprises a stationary ring 53, which is preferably the inner ring 53 of the bearing 50, which holds the containment 12 blocked against the base 15 by way of the inner lip 16 of the containment 12.

The biopharmaceutical liquid 3 comprises inert micro-supports (not represented in FIG. 1, but they are evenly distributed within the biopharmaceutical liquid 3), of which the largest dimension is less than 0.3 mm, preferably less than 0.1 mm, advantageously greater than 10 µm, for example comprised between 30 µm and 80 µm. Living cells are fastened to these micro-supports. These micro-supports are advantageously balls. The volume of the bag 1 can go from a few tens of liters to a few thousands of liters of biopharmaceutical liquid 3, preferably 50 to 2000 liters of biopharmaceutical liquid 3. For example, every 3 weeks or every month, the bag 1 undergoes a partial draining and a sampling of the cell medium cultivated in the bag 1. The wall of the bag 1 is made of sufficiently flexible and deformable material to be able to be folded, for example the wall of the bag 1 is made of flexible plastic.

Most of the parts of the sets are made of rigid plastic, slightly deformable so as to be able to carry out an operation of clipping to one another, are preferably made of polyethylene (PE), advantageously made of high-density polyethylene (HDPE), or made of polyethylene terephthalate (PET). Except for the bearing 50, which can be made of metal, all the other parts of the mechanical member 4 can advantageously be made by injection molding. Preferably, all the parts of the rotating 30 and stationary 10 sets can be made without a thread, without glue, and be assembled to one another simply by clipping. A sealing lip 40 directly overmolded on the cap 32, allows to ensure the sealing with the rotating shaft 31, in particular when this rotates, as the cap 32 is integral with the rotating shaft 31 and rotates with it.

FIG. 2 schematically represents an overall perspective, cross-sectional view of an optional detail of an example of assembly of stationary and rotating sets of the mechanical member of the biopharmaceutical liquid vessel according to a first embodiment of the invention.

FIG. 2 shows fins 113 regularly distributed about the axis of rotation 31 in the branch 63 of the communication passage 60 forming the inverted siphon 61, these fins 113 extending perpendicularly to the inner face 111 of the outer wall 110 of the cap 32 of the rotating set 30, these fins 113 being flat plates parallel to the axis of rotation 31.

There are around between 8 and 15 fins regularly distributed about the axis of rotation 31. These fins 113 extend over half of the width l of the branch 63 of the communication passage 60. These fins 113 are advantageously integrally made with the inner face 111 of the outer wall 110 of the cap 32, but alternatively they can be separate plates welded on the inner face 111 of the outer wall 110 of the cap 32. The fins 113 do not exceed to the bottom of the outer wall 110 of the cap 32, they are advantageously stopped before the end of this wall.

FIG. 3 schematically represents an overall perspective, cross-sectional view of an optional detail of an example of assembly of stationary and rotating sets of the mechanical member of the biopharmaceutical liquid vessel according to a first embodiment of the invention.

FIG. 3 shows fins 114 regularly distributed about the axis of rotation 31 in the branch 63 of the communication passage 60 forming the inverted siphon 61, these fins 114 extending perpendicularly to the inner face 111 of the outer wall 110 of the cap 32 of the rotating set 30, these fins 114 being curved and inclined plates mainly with respect to the axis of rotation 31 with an acute angle, preferably less than 30 degrees, advantageously of the order of 15 degrees. These fins 114 could also be straight plates inclined with respect to the axis of rotation 31 with an acute angle, preferably less than 30 degrees, advantageously of the order of 15 degrees.

There are around between 8 and 15 fins 114 regularly distributed about the axis of rotation 31. These fins 114 extends over half of the width l of the branch 63 of the communication passage 60. These fins 114 are advantageously integrally made with the inner face 111 of the outer wall 110 of the cap 32, but alternatively they can be separate plates welded on the inner face 111 of the outer wall 110 of the cap 32. The fins 114 do not exceed to the bottom of the outer wall 110 of the cap 32, they are advantageously stopped before the end of this wall.

FIG. 4 schematically represents an overall perspective, cross-sectional view of the optional detail of an example of assembly of the stationary and rotating sets of the mechanical member of the biopharmaceutical liquid vessel according to a first embodiment of the invention.

FIG. 4 shows fins 115 regularly distributed about the axis of rotation 31 in the branch 63 of the communication passage 60 forming the inverted siphon 61, these fins 115 extending perpendicularly to the outer face 112 of the projection 18 of the stationary set 10, these fins 115 being straight plates parallel to the axis of rotation 31.

There are around between 8 and 15 fins 115 regularly distributed about the axis of rotation 31. These fins 115 extend over half of the width 1 of the branch 63 of the communication passage 60. These fins 115 are advantageously integrally made with the outer face 112 of the projection 18, but alternatively they can be separate plates welded on the outer face 112 of the projection 18. The fins 115 rest on the small projection 17.

FIG. 5 schematically represents an overall perspective, cross-sectional view of an optional detail of an example of assembly of stationary and rotating sets of the mechanical member of the biopharmaceutical liquid vessel according to a first embodiment of the invention.

FIG. 5 shows fins 116 regularly distributed about the axis of rotation 31 in the branch 63 of the communication passage 60 forming the inverted siphon 61, these fins 116 extending perpendicularly to the outer face 112 of the projection 18 of the stationary set 10, these fins 116 being straight plates inclined with respect to the axis of rotation 31 with an acute angle, preferably less than 30 degrees, advantageously of the order of 15 degrees. These fins 116 could also be curved and inclined plates mainly with respect to the axis of rotation 31 with an acute angle, preferably less than 30 degrees, advantageously of the order of 15 degrees.

There are around between 8 and 15 fins 116 regularly distributed about the axis of rotation 31. These fins 116 extend over half of the width 1 of the branch 63 of the communication passage 60. These fins 116 are advantageously integrally made with the outer face 112 of the projection 18, but alternatively they can be separate plates welded on the outer face 112 of the projection 18. The fins 116 rest on the small projection 17.

FIG. 6 schematically represents an overall perspective, cross-sectional view of an optional detail of an example of assembly of the stationary and rotating sets of the mechanical member of the biopharmaceutical liquid vessel according to a first embodiment of the invention.

FIG. 6 shows fins 117 regularly distributed about the axis of rotation 31 in the branch 63 of the communication passage 60 forming the inverted siphon 61, these fins 117 extending in an inclined manner with respect to the outer face 112 of the projection 18 of the stationary set 10, the direction of the inclination being such as given the direction of rotation of the rotating set 30 around the stationary set 10 of possible solid particles located in the branch 63 of the communication passage 60 remain retained or blocked between the fins 117 and the outer wall 112 of the projection 18, these fins 117 being straight plates parallel to the axis of rotation 31.

There are around between 8 and 15 fins 117 regularly distributed about the axis of rotation 31. These fins 117 extend over half of the width 1 of the branch 63 of the communication passage 60. These fins 117 are advantageously integrally made with the outer face 112 of the projection 18, but alternatively they can be separate plates welded on the outer face 112 of the projection 18. The fins 117 rest on the small projection 17.

FIG. 7 schematically represents an overall exploded perspective, cross-sectional view of an example of assembly of the stationary and rotating sets of the mechanical member of the biopharmaceutical liquid vessel according to a first embodiment of the invention.

The cap 32 enters into the intermediate part 34. The gas distributor 20 is directly clipped on the base 15. The intermediate part 34 enters into the containment 12 which enters into the base 15. The connecting part 14 enters into the draining port 11, passes through the base 15 until arriving at the top of the funnel 19, thus fastening the rotating set 30 with respect to the stationary set 10, the bearing 50 being blocked, on the one hand at the top by the outer radial lugs located at the top of the funnel 19 and, on the other hand, at the bottom by the inner lip 16 of the containment 12.

FIG. 8 schematically represents an overall perspective view of an example of assembly of the stationary and rotating sets of the mechanical member of the biopharmaceutical liquid vessel according to a first embodiment of the invention. The mechanical member 4 is in a completely mounted position.

FIG. 9 schematically represents an overall perspective, cross-sectional view of an example of a rotating set of the mechanical member of the biopharmaceutical liquid vessel according to a first embodiment of the invention.

In a first step of mounting the mechanical member 4, the rotating shaft 31 is first press-fitted in the cap 32, thanks to a certain flexibility of the sealing lip 40 (which can be made of LLDPE, for example).

In a second step of mounting the mechanical member 4, the bearing 50 is clipped in the bottom of the intermediate part 34, advantageously using a tool or by simple manual pressure. The intermediate part has both a good rigidity and a little flexibility at the clips thereof in the bottom portion under the outer ring 52 of the bearing 50.

FIG. 10 schematically represents a local perspective view of a portion of a rotating set of the mechanical member of the biopharmaceutical liquid vessel according to a first embodiment of the invention.

The inner bottom crown of the intermediate connecting part 34 comprises on the inner surface thereof, six projections disposed to absorb the manufacturing tolerances and avoid a free rotation between the outer ring 52 of the bearing 50 on the one hand, and this inner crown of the intermediate part 34 wherein the bearing 50 is precisely housed.

FIG. 11 schematically represents an overall perspective, cross-sectional view of an example of assembly of a rotating set of the mechanical member of the biopharmaceutical liquid vessel according to a first embodiment of the invention.

In a third step of mounting the mechanical member 4, the rotating shaft 31 carrying the cap 32 enters into the top portion of the intermediate connecting part 34 so as to be clipped inside, by outer radial lugs located in the bottom portion of the rotating shaft 31, engaging with cavities located in the median portion of the intermediate connecting part 34.

FIG. 12 schematically represents a local perspective view of a portion of an example of a rotating set of the mechanical member of the biopharmaceutical liquid vessel according to a first embodiment of the invention.

FIG. 13 schematically represents a local perspective view of an example of a rotating set of the mechanical member of the biopharmaceutical liquid vessel according to a first embodiment of the invention.

The intermediate connecting part 34 has a flat piece 38 which will engage with the flat piece 39 of the rotating shaft 31, to block the relative rotation of the rotating shaft 31 with respect to the intermediate connecting part 34.

The top inner crown of the intermediate connecting part 34 comprises on the inner surface thereof, four projections disposed to absorb the manufacturing tolerances and avoid a free rotation between the rotating shaft 31 on the one hand, and this inner crown of the intermediate part 34 wherein the rotating shaft 31 is precisely housed.

FIG. 14 schematically represents an overall perspective, cross-sectional view of an example of a rotating set of the mechanical member of the biopharmaceutical liquid vessel according to a first embodiment of the invention.

In a fourth step of mounting the mechanical member 4, the cap 32, located around the rotating shaft 31, slides around the rotating shaft 31 by descending to abutting against the projection of the intermediate connecting part 34, this projection being located at the junction between the top crown and the bottom crown of this intermediate connecting part 34.

FIG. 15 schematically represents a local perspective view of an example of a portion of a rotating set of the mechanical member of the biopharmaceutical liquid vessel according to a first embodiment of the invention.

FIG. 16 schematically represents a local perspective view of an example of a portion of a rotating set of the mechanical member of the biopharmaceutical liquid vessel according to a first embodiment of the invention.

On the outer bottom crown of the intermediate connecting part 34 are distributed eight small cavities engaging with the eight small projections distributed on the bottom inner surface of the cap 32, to clip the cap 32 on the outside of the intermediate connecting part 34.

FIG. 17 schematically represents an overall perspective, cross-sectional view of an example of a stationary set of the mechanical member of the biopharmaceutical liquid vessel according to a first embodiment of the invention.

In a fifth step of mounting of the mechanical member 4, the gas distributor 20 is clipped around the base 15 thanks to the outer radial lugs of the base 15 located in the top portion of the periphery of the base 15.

FIG. 18 schematically represents an overall perspective, cross-sectional view of an example of a stationary set of the mechanical member of the biopharmaceutical liquid vessel according to a first embodiment of the invention.

In a sixth step of mounting the mechanical member 4, the containment 1 is entered up to the bottom of the receptacle of the base 15. The trough 17 located in the outer median portion of the containment 12 pushes the upper outer radial lugs of the base 15, thus contributing to maintaining the clipping of the gas distributor 20 around the outer periphery of the base 15.

FIG. 19 schematically represents a local perspective, cross-sectional view of an example of a portion of a stationary set of the mechanical member of the biopharmaceutical liquid vessel according to a first embodiment of the invention.

The inner lip 16 ensures, on the one hand, the holding of the containment 12 in the bottom of the receptacle of the base 15 until the following mounting step, the once the mounting has ended, will contribute to ensuring the sealing between the containment 12 and the base 15.

FIG. 20 schematically represents an overall perspective, cross-sectional view of an example of a stationary set of the mechanical member of the biopharmaceutical liquid vessel according to a first embodiment of the invention.

In a seventh step of mounting the mechanical member 4, the bearing 50 is clipped around the funnel 19 of the base 15, thanks to the outer radial lugs of the top portion of this funnel 19.

FIG. 21 schematically represents a local perspective, cross-sectional view of an example of a portion of a stationary set of the mechanical member of the biopharmaceutical liquid vessel according to a first embodiment of the invention.

The clipping of the bearing 50 around the funnel 19 will be even more easily done by using low-density polyethylene (LLDPE) for the funnel 19, at least partially.

FIG. 22 schematically represents an overall perspective, cross-sectional view of an example of a stationary set of the mechanical member of the biopharmaceutical liquid vessel according to a first embodiment of the invention.

In an eighth step of mounting the mechanical member 4, the fastening part 14 is introduced through the draining port 11 until it arrives in the funnel 19. The fastening part 14 will be preferably press-fitted in the base 15 with a manual tool having a stop position to be certain of having actually press-fitted this connecting part 14 up to the top of the funnel 19.

FIG. 23 schematically represents an overall perspective, cross-sectional view of an example of assembly of stationary and rotating sets of the mechanical member of the biopharmaceutical liquid vessel according to a first embodiment of the invention, showing the diversion connecting the gas distributor and the communication passage.

A diversion 21 connects the inside of the gas distributor 20 to the inside of the communication passage 60. The function of this diversion 21 is to be able to blow air into the communication passage 60 so as to tend to make it emerge into the inner storage space 2. In the preferable embodiment of FIG. 23, this diversion channel 21, on the one hand, opens to one of the ends thereof in the ring forming the inside of the gas distributor 20, and more specifically in the inner wall thereof, and on the other hand, opens to the other of the ends thereof in the branch 64 starting at the bottom 62 of the inverted siphon 61 and going up to the bearing 50, and more specifically in the outer wall thereof. The inner and outer walls are defined with respect to the center of symmetry of the vessel, the inner wall of a given element being radially closer to this center of symmetry than the outer wall of this element.

FIG. 24 schematically represents an overall perspective, cross-sectional view of an example of assembly of the stationary and rotating sets of the mechanical member of the biopharmaceutical liquid vessel according to a second embodiment of the invention. The second embodiment is similar to the first embodiment, except for in certain aspects mentioned below in the text.

FIG. 25 schematically represents an overall exploded perspective, cross-sectional view of an example of assembly of stationary and rotating sets of the mechanical member of the biopharmaceutical liquid vessel according to a second embodiment of the invention.

The intermediate connecting part 34 and the fastening part 14 have been replaced by a central trunk 36 of which the top portion is surrounded by the inner ring 53 of the bearing 50 and covered by an upper part 35 resting on the top of the outer ring 52 of the bearing 50, the bottom portion of the central trunk 36 being surrounded by a lower ring 13. The central trunk 36 and the lower ring 13 belong to the stationary set 10, while the upper part 35 belongs to the rotating set 30. The outer ring 52 of the bearing 50 remains integral with the rotating set 30, while the inner ring 53 of the bearing 50 remains integral with the stationary set 10. The upper part 35 has holes to limit the dead zones. In the stationary set 10, from the center to the periphery, the central trunk 36 pushes radially on the lower ring 13 which pushes radially on the funnel 19 of the base 15, which funnel (visible only in FIG. 25 but not in FIG. 24) pushes radially on the containment 12 which pushes radially on the periphery of the base 15.

FIG. 26 schematically represents an overall perspective view of an example of a stationary and rotating sets of the mechanical member of the biopharmaceutical liquid vessel according to a second embodiment of the invention. The mechanical member 4 is represented in a completely mounted position.

FIG. 27 schematically represents an overall perspective, cross-sectional view of an example of a stationary set of the mechanical member of the biopharmaceutical liquid vessel according to a second embodiment of the invention.

FIG. 28 schematically represents a local perspective, cross-sectional view of an example of a portion of assembly of a stationary set of the mechanical member of the biopharmaceutical liquid vessel according to a second embodiment of the invention.

In a first step of mounting the mechanical member 4, the lower ring 13 is clipped inside the central funnel 19 of the base 15. Peripheral projections inclined conically in the direction of the penetration and disposed on the outer surface of the lower ring 13 are clipped in corresponding holes of the central funnel 19 of the base 15.

FIG. 29 schematically represents an overall perspective, cross-sectional view of an example of a rotating set of the mechanical member of the biopharmaceutical liquid vessel according to a second embodiment of the invention.

FIG. 30 schematically represents a local perspective, cross-sectional view of an example of a portion of a rotating set of the mechanical member of the biopharmaceutical liquid vessel according to a second embodiment of the invention.

In a second step of mounting the mechanical member 4, the bearing 50 is clipped around the central trunk 36, and more specifically around outer tabs having outer radial lugs, the inner ring 53 of the bearing 50 being blocked between these outer radial lugs of these outer tabs of the central trunk 36 and the inner lip 16 of the containment 12. The bottom portion of the central trunk 36 comprises four peripheral projections so as to avoid a free rotation between the central trunk 36 and the lower ring 13.

FIG. 31 schematically represents an overall perspective, cross-sectional view of an example of a rotating set of the mechanical member of the biopharmaceutical liquid vessel according to a second embodiment of the invention.

FIG. 32 schematically represents a local perspective, cross-sectional view of an example of a rotating set of the mechanical member of the biopharmaceutical liquid vessel according to a second embodiment of the invention.

In a third step of mounting the mechanical member 4, the upper part 35 is clipped, through the annular projection thereof in the bottom portion, in the inner wall of the cap 32 which comprises eight small projections to absorb the manufacturing tolerances and prevent a free rotation in the cap 32, both of the upper part 35 and of the outer ring 52 of the bearing 50.

FIG. 33 schematically represents an overall perspective, cross-sectional view of an example of a stationary set of the mechanical member of the biopharmaceutical liquid vessel according to a second embodiment of the invention.

In a fourth step of mounting the mechanical member 4, the rotating shaft (not represented in FIG. 33) is press-fitted in the upper part 35.

In a fifth step of mounting the mechanical member 4, the gas distributor (not represented in FIG. 33) is clipped around the remainder of the mechanical member 4.

In a sixth step of mounting the mechanical member 4, the mechanical member 4 is fastened inside the opening of the wall of the bag 1.

Of course, the present invention is not limited to the examples and to the embodiment described and represented, but it can have numerous variants accessible to a person skilled in the art.

The invention claimed is:

1. A biopharmaceutical liquid vessel, comprising:
   a bag forming an inner storage space for storing biopharmaceutical liquid,
   a mechanical member located at a wall of the bag, comprising:
   a set of stationary parts, stationary with respect to the wall of the bag,
   a set of rotating parts, rotating about an axis of rotation with respect to the set of stationary parts,
   a bearing located between the set of stationary parts and the set of rotating parts and in an inner storage space inside the bag,
   a communication passage separating the bearing of the inner storage space, comprising one or more changes of direction being formed by a portion of the parts of the set of rotating parts located opposite a portion of the parts of the set of stationary parts.

2. The biopharmaceutical liquid vessel according to claim 1, wherein the passage forms an inverted siphon, of the air being trapped in a bottom of the inverted siphon by the liquid located at least in one branch of the inverted siphon starting at the bottom of the inverted siphon and opening into the inner storage space.

3. The biopharmaceutical liquid vessel according to claim 2, wherein said air being trapped in the bottom of the inverted siphon by the liquid located at least in two branches of the at least one branch of the inverted siphon, a first branch of the two branches starting at the bottom of the inverted siphon and opening into the inner storage space and a second branch of the two branches starting at the bottom of the inverted siphon and going up to the bearing.

4. The biopharmaceutical liquid vessel according to claim 2, wherein the bearing is an only contact zone between the set of rotating parts and the set of stationary parts.

5. The biopharmaceutical liquid vessel according to claim 1, wherein the communication passage travels mainly between a cap of the set of rotating parts and a containment of the set of stationary parts, the cap rotating about the axis of rotation with respect to the containment, the cap and the containment being nested at least partially in one another to form the communication passage.

6. The biopharmaceutical liquid vessel according to claim 1, wherein the set of stationary parts or the set of rotating parts forms a projection entering into a cavity of the other set, the communication passage bypassing the projection by traveling along the walls of the cavity.

7. The biopharmaceutical liquid vessel according to claim 6, wherein the set of rotating parts forms the cavity and the set of stationary parts forms the projection.

8. The biopharmaceutical liquid vessel according to claim 1, wherein the communication passage is a passage having a symmetry of revolution about the axis of rotation.

9. The biopharmaceutical liquid vessel according to claim 1, wherein the width of the communication passage in a plane containing the axis of rotation is comprised between 0.5 mm and 5 mm.

10. The biopharmaceutical liquid vessel according to claim 1, wherein the communication passage comprises at least two passages parallel to the axis of rotation, separated by a bend.

11. The biopharmaceutical liquid vessel according to claim 10, wherein one of the passages parallel to the axis of rotation connects the bend to a cavity comprising the bearing.

12. The biopharmaceutical liquid vessel according to claim 1, wherein the communication passage comprises radial fins regularly distributed about the axis of rotation, located in the branch of the inverted siphon starting at the bottom of the inverted siphon and opening into the inner storage space.

13. The biopharmaceutical liquid vessel according to claim 12, wherein the radial fins extend from the outer face of the inner wall of a portion of the set of stationary parts.

14. The biopharmaceutical liquid vessel according to claim 12, wherein the radial fins extend in an inclined manner with respect to a wall inside the communication passage, the direction of the inclination being such as given from the direction of rotation of the set of rotating parts around the set of stationary parts of possible solid particles located in the communication passage remain retained or blocked between the fins and said wall inside the communication passage.

15. The biopharmaceutical liquid vessel according to claim 1, wherein the bearing is an only support zone of the set of rotating parts by the set of stationary parts.

16. The biopharmaceutical liquid vessel according to claim 1, wherein the bearing is a ball bearing.

17. The biopharmaceutical liquid vessel according to claim 1, wherein the mechanical member passes through the wall of the bag at an opening of the wall of the bag.

18. The biopharmaceutical liquid vessel according to claim 17, wherein the opening of the wall of the bag is fastened in a sealed manner around the mechanical member.

19. The biopharmaceutical liquid vessel according to claim 18, wherein the opening is welded or glued around the set of stationary parts.

20. The biopharmaceutical liquid vessel according to claim 1, wherein the set of rotating parts carries a rotating shaft.

21. The biopharmaceutical liquid vessel according to claim 20, wherein the rotating shaft carries a propeller.

22. The biopharmaceutical liquid vessel according to claim 1, wherein set of stationary parts comprises a draining port opening to an outside of the bag.

23. The biopharmaceutical liquid vessel according to claim 1, wherein a gas distributor is located around the set of stationary parts and the set of rotating parts, in the inner storage space.

24. The biopharmaceutical liquid vessel according to claim 23, wherein the gas distributor is annular.

25. The biopharmaceutical liquid vessel according to claim 23, wherein the gas distributor comprises at least one diversion capable of blowing air into the communication passage so as to tend to make the air emerge in the inner storage space.

26. The biopharmaceutical liquid vessel according to claim 1, wherein the set of rotating parts comprises an intermediate connecting part carrying the rotating shaft and the bearing.

27. The biopharmaceutical liquid vessel according to claim 26, wherein the rotating shaft is clipped in the intermediate connecting part.

28. The biopharmaceutical liquid vessel according to claim 26, wherein the bearing comprises an outer ring, said outer ring clipped in the intermediate connecting part.

29. The biopharmaceutical liquid vessel according to claim 26, wherein the intermediate connecting part carries the rotating cap which is clipped on this intermediate connecting part.

30. The biopharmaceutical liquid vessel according to claim 1, wherein the stationary set comprises a base which carries the bearing, and which has a draining port opening to an outside of the inner storage space.

31. The biopharmaceutical liquid vessel according to claim 30, wherein the gas distributor is clipped around the base.

32. The biopharmaceutical liquid vessel according to claim 30, wherein the bearing is clipped around the base.

33. The biopharmaceutical liquid vessel according to claim 30, wherein the bearing comprises a stationary inner ring, said inner ring maintaining the containment blocked against the base.

34. The biopharmaceutical liquid vessel according to claim 1, wherein the biopharmaceutical liquid comprises inert micro-supports, of which the largest dimension is less than 0.3 mm cells fastened to these micro-supports.

35. The biopharmaceutical liquid vessel according to claim 34, wherein the micro-supports are balls.

36. The biopharmaceutical liquid vessel according to claim 1, wherein most of the parts of the set of stationary parts and the set of rotating parts are made of rigid plastic, slightly deformable so as to be able to carry out an operation of clipping to one another.

37. The biopharmaceutical liquid vessel according to claim 1, wherein the wall of the bag is made of material, sufficiently flexible and deformable to be able to be folded.

* * * * *